(12) United States Patent
Conner et al.

(10) Patent No.: US 11,589,616 B2
(45) Date of Patent: Feb. 28, 2023

(54) AEROSOL DELIVERY DEVICE WITH SLIDING AND AXIALLY ROTATING LOCKING MECHANISM

(71) Applicant: R.J. REYNOLDS TOBACCO COMPANY, Winston-Salem, NC (US)

(72) Inventors: Billy T. Conner, Clemmons, NC (US); Thaddeus Jackson, Summerfield, NC (US); Taylor Leigh, Alpharetta, GA (US); Randall Bachtel, Lawrenceville, GA (US); Frank Bascas, Montezuma, GA (US); Hannah Tam, San Francisco, CA (US); Moises Araya, Atlanta, GA (US); Nigel J. Flynn, Flowery Branch, GA (US)

(73) Assignee: R.J. REYNOLDS TOBACCO COMPANY, Winston-Salem, NC (US)

( * ) Notice: Subject to any disclaimer, the term of this patent is extended or adjusted under 35 U.S.C. 154(b) by 351 days.

(21) Appl. No.: 16/861,713

(22) Filed: Apr. 29, 2020

(65) Prior Publication Data

US 2021/0337864 A1 Nov. 4, 2021

(51) Int. Cl.
*A24F 40/42* (2020.01)
*A24F 40/485* (2020.01)
(Continued)

(52) U.S. Cl.
CPC ............ *A24F 40/42* (2020.01); *A24F 40/485* (2020.01); *A61M 11/041* (2013.01);
(Continued)

(58) Field of Classification Search
CPC .......... A24F 42/10; A24F 40/46; A24F 40/42; A24F 40/485; A24F 13/14; A24F 13/02;
(Continued)

(56) References Cited

U.S. PATENT DOCUMENTS 1,464,300 A 8/1923 Taff
1,505,655 A 8/1924 Marek
(Continued)

FOREIGN PATENT DOCUMENTS

EP 2 022 349 A1 11/2009
JP 2002034543 A 2/2002
(Continued)

OTHER PUBLICATIONS

Stephenson, "A 'Safer' Cigarette? Prove It, Say Critics", JAMA, 2000, 283(19), pp. 2507-2508. doi:10.1001/jama.283.19.2507.
(Continued)

*Primary Examiner* — Vishal Pancholi
*Assistant Examiner* — Robert K Nichols, II
(74) *Attorney, Agent, or Firm* — Womble Bond Dickinson (US) LLP

(57) ABSTRACT

The present disclosure is directed to an aerosol delivery device and a holder for use with a removable substrate cartridge. In one implementation, the holder includes a first body portion and a second body portion, the first body portion defining a main body and a guide post that defines a receiving chamber extending at least a portion therethrough. The second body portion is configured to rotate about and slide along at least a portion of the guide post to and from a use position, wherein the second body portion is proximate the main body of the first body portion and the substrate cartridge is retained in the receiving chamber, and an open position, wherein the second body portion is rotated relative to and extended away from the main body of the first body portion such that the substrate cartridge can be inserted into or removed from the receiving chamber.

20 Claims, 8 Drawing Sheets

(51) Int. Cl.
*A61M 11/04* (2006.01)
*A61M 15/00* (2006.01)
*B05B 11/00* (2023.01)

(52) U.S. Cl.
CPC ....... *A61M 15/009* (2013.01); *B05B 11/0002* (2013.01); *B05B 11/0054* (2013.01); *A61M 2205/364* (2013.01)

(58) Field of Classification Search
CPC .............. A61M 11/041; A61M 15/009; A61M 2205/364; B05B 11/0002; B05B 11/0054; A24D 1/22
See application file for complete search history.

(56) References Cited

U.S. PATENT DOCUMENTS

| | | |
|---|---|---|
| 1,541,891 A | 6/1925 | Becker |
| 1,607,132 A | 11/1926 | Kuno |
| 1,613,545 A | 1/1927 | Teigen |
| 1,941,531 A | 1/1934 | Blankenship |
| 2,008,433 A | 7/1935 | Ashour |
| 2,373,629 A | 4/1945 | Kilgore |
| 2,455,492 A | 12/1948 | Jackson |
| 2,502,831 A | 4/1950 | Daze |
| 2,541,837 A | 2/1951 | Schroff |
| 2,701,571 A | 2/1955 | Dittrich |
| 2,711,176 A | 6/1955 | Vakilian |
| 2,779,340 A | 1/1957 | Mansfield |
| 2,953,136 A | 9/1960 | Dahly |
| 3,155,099 A | 11/1964 | Minchin |
| 3,181,538 A | 5/1965 | Piliego |
| 3,685,520 A | 8/1972 | Chernack |
| 4,708,151 A | 11/1987 | Shelar |
| 4,714,082 A | 12/1987 | Banerjee et al. |
| 4,966,171 A | 10/1990 | Serrano et al. |
| 4,991,606 A | 2/1991 | Serrano et al. |
| 5,040,552 A | 8/1991 | Schleich et al. |
| 5,060,676 A | 10/1991 | Hearn et al. |
| 5,076,296 A | 12/1991 | Nystrom et al. |
| 5,159,940 A | 11/1992 | Hayward et al. |
| 5,178,165 A | 1/1993 | DeFelice |
| 5,240,012 A | 8/1993 | Ehrman et al. |
| 5,592,955 A | 1/1997 | Keritsis |
| 5,595,577 A | 1/1997 | Bensalem et al. |
| 5,692,525 A | 12/1997 | Counts et al. |
| 5,845,649 A | 12/1998 | Saito et al. |
| 6,006,757 A | 12/1999 | Lichtenberg |
| 6,053,176 A | 4/2000 | Adams et al. |
| 6,164,287 A | 12/2000 | White |
| 6,311,694 B1 | 11/2001 | Nichols et al. |
| 6,345,625 B1 | 2/2002 | Chew |
| 6,371,127 B1 | 4/2002 | Snaidr et al. |
| 6,431,177 B1 | 8/2002 | Sieggen et al. |
| 6,532,965 B1 | 3/2003 | Abhulimen et al. |
| 6,615,843 B2 | 9/2003 | Pera |
| 6,748,955 B2 | 6/2004 | Snaidr et al. |
| 7,080,649 B2 | 7/2006 | Hcu |
| 7,503,330 B2 | 3/2009 | Borschke et al. |
| 7,600,517 B1 | 10/2009 | Holzrichter |
| 7,624,739 B2 | 12/2009 | Snaidr et al. |
| 8,061,361 B2 | 11/2011 | Maeder et al. |
| 8,151,803 B2 | 4/2012 | Inagaki |
| 8,302,611 B2 | 11/2012 | Rowley |
| 8,528,567 B2 | 9/2013 | Hajaligol |
| 8,616,217 B2 | 12/2013 | Tsurizumi et al. |
| 8,776,803 B2 | 7/2014 | Tarora et al. |
| 8,863,754 B2 | 10/2014 | Renaud et al. |
| 8,915,255 B2 | 12/2014 | Poget et al. |
| 9,078,473 B2 | 7/2015 | Worm et al. |
| 9,149,072 B2 | 10/2015 | Conner et al. |
| 9,220,301 B2 | 12/2015 | Banerjee et al. |
| 9,282,769 B2 | 3/2016 | Mishra et al. |
| 9,301,546 B2 | 4/2016 | Thomas et al. |
| 9,332,784 B2 | 5/2016 | Banerjee et al. |
| 9,439,453 B2 | 9/2016 | Conner et al. |
| 9,532,591 B2 | 1/2017 | Mironov |
| 9,549,572 B2 | 1/2017 | Dincer et al. |
| 9,609,893 B2 | 4/2017 | Novak, III et al. |
| 9,629,393 B2 | 4/2017 | Stolz et al. |
| 9,693,587 B2 | 7/2017 | Plojoux |
| 9,717,273 B2 | 8/2017 | Poget et al. |
| 9,730,468 B2 | 8/2017 | Poget et al. |
| 9,801,412 B2 | 10/2017 | Grant |
| 9,894,930 B2 | 2/2018 | Bonici et al. |
| 9,918,494 B2 | 3/2018 | Mironov et al. |
| 9,930,915 B2 | 4/2018 | Worm et al. |
| 9,943,114 B2 | 4/2018 | Batista |
| 9,961,939 B2 | 5/2018 | Reevell |
| 10,034,493 B2 | 7/2018 | Akiyama et al. |
| 10,064,428 B2 | 9/2018 | Swepston et al. |
| 10,064,478 B2 | 9/2018 | Brooks |
| 10,111,463 B2 | 10/2018 | Batista |
| 10,159,277 B2 | 12/2018 | Bonnely |
| 10,212,968 B2 | 2/2019 | Mironov et al. |
| 10,398,168 B2 | 9/2019 | Maiwald et al. |
| 10,470,491 B2 | 11/2019 | Sutton et al. |
| 10,492,526 B2 | 12/2019 | Sampson et al. |
| 10,524,503 B2 | 1/2020 | Florack et al. |
| 10,827,780 B2 | 11/2020 | Swepston et al. |
| 2008/0047570 A1 | 2/2008 | Plank |
| 2009/0065011 A1 | 3/2009 | Maeder et al. |
| 2011/0083674 A1 | 4/2011 | Karpinsky |
| 2013/0133675 A1 | 5/2013 | Shinozaki et al. |
| 2013/0167850 A1 | 7/2013 | Al-Aawar |
| 2013/0228190 A1 | 9/2013 | Weiss et al. |
| 2014/0048085 A1 | 2/2014 | Cox |
| 2015/0034100 A1 | 2/2015 | Park et al. |
| 2015/0040924 A1 | 2/2015 | Mironov et al. |
| 2015/0296882 A1 | 10/2015 | Mironov et al. |
| 2015/0342254 A1 | 12/2015 | Mironov et al. |
| 2016/0007648 A1 | 1/2016 | Sutton et al. |
| 2016/0007649 A1 | 1/2016 | Sampson et al. |
| 2016/0073692 A1 | 3/2016 | Alarcon et al. |
| 2016/0120216 A1 | 5/2016 | Mironov et al. |
| 2016/0135495 A1 | 5/2016 | Poget et al. |
| 2016/0174609 A1 | 6/2016 | Mironov |
| 2016/0192704 A1 | 7/2016 | Bonnely |
| 2016/0316816 A1 | 11/2016 | Lavanchy et al. |
| 2016/0360785 A1 | 12/2016 | Bless et al. |
| 2017/0000189 A1 | 1/2017 | Mironov et al. |
| 2017/0055577 A1 | 3/2017 | Batista |
| 2017/0055578 A1 | 3/2017 | Oda et al. |
| 2017/0164654 A1 | 6/2017 | Ademe |
| 2017/0196261 A1 | 7/2017 | Borges De Couraca et al. |
| 2017/0303585 A1 | 10/2017 | Florack et al. |
| 2017/0318859 A1 | 11/2017 | Batista |
| 2018/0000165 A1 | 1/2018 | Liu |
| 2018/0014571 A1 | 1/2018 | Nakano |
| 2018/0070640 A1 | 3/2018 | Bessant et al. |
| 2018/0116280 A1 | 5/2018 | Maiwald et al. |
| 2018/0192707 A1 | 7/2018 | Worm et al. |
| 2018/0317560 A1 | 11/2018 | Shinozaki et al. |
| 2018/0325167 A1 | 11/2018 | Grant |
| 2018/0368468 A1 | 12/2018 | Mishra et al. |
| 2019/0000135 A1 | 1/2019 | Lavanant et al. |
| 2019/0000141 A1 | 1/2019 | Rojo-Calderon et al. |
| 2019/0000142 A1 | 1/2019 | Lavanchy et al. |
| 2019/0014818 A1* | 1/2019 | Saygili .................... A24F 13/02 |
| 2019/0014820 A1 | 1/2019 | Malgat |
| 2019/0014821 A1 | 1/2019 | Batista et al. |
| 2019/0059449 A1 | 2/2019 | Akiyama et al. |
| 2019/0059450 A1 | 2/2019 | Akiyama et al. |
| 2019/0075848 A1 | 3/2019 | Worm et al. |
| 2019/0124972 A1 | 5/2019 | Nakano |
| 2019/0124973 A1 | 5/2019 | Nakano et al. |
| 2019/0133176 A1 | 5/2019 | Nakano et al. |
| 2019/0150505 A1 | 5/2019 | Ceppi et al. |
| 2019/0274358 A1 | 9/2019 | Reevell |
| 2020/0015519 A1 | 1/2020 | Conner et al. |
| 2020/0060333 A1 | 2/2020 | Sutton et al. |
| 2020/0146349 A1 | 5/2020 | Phillips et al. |
| 2020/0268044 A1 | 8/2020 | Wilson |

(56) References Cited

U.S. PATENT DOCUMENTS

2021/0015172 A1  1/2021  Conner et al.
2021/0015174 A1  1/2021  Cox et al.
2021/0015175 A1  1/2021  Jackson et al.

FOREIGN PATENT DOCUMENTS

| WO | WO1995034226 | 12/1995 |
|---|---|---|
| WO | WO1998054989 | 12/1998 |
| WO | WO2009022232 | 2/2009 |
| WO | WO2013072336 | 5/2013 |
| WO | 2013083963 A1 | 6/2013 |
| WO | WO2013149810 | 10/2013 |
| WO | WO2013189836 | 12/2013 |
| WO | WO2014037270 | 3/2014 |
| WO | WO2014156838 | 10/2014 |
| WO | 2014180893 A1 | 11/2014 |
| WO | WO2015097005 | 7/2015 |
| WO | WO2015128384 | 9/2015 |
| WO | WO2015151158 | 10/2015 |
| WO | WO2015184744 | 12/2015 |
| WO | WO2015197850 | 12/2015 |
| WO | WO2017042297 | 3/2017 |
| WO | WO2017108912 | 6/2017 |
| WO | WO2017114760 | 7/2017 |
| WO | WO2017115181 | 7/2017 |
| WO | WO2017115182 | 7/2017 |
| WO | WO2017115183 | 7/2017 |
| WO | WO2017115184 | 7/2017 |
| WO | WO2017115185 | 7/2017 |
| WO | WO2017115188 | 7/2017 |
| WO | WO2017115196 | 7/2017 |
| WO | WO2017207442 | 12/2017 |
| WO | WO2017212284 | 12/2017 |
| WO | WO2018170800 | 9/2018 |
| WO | WO2018201655 | 11/2018 |
| WO | WO2019010680 | 1/2019 |
| WO | 2019/148481 A1 | 8/2019 |
| WO | 2019/243612 A1 | 12/2019 |
| WO | 2020216762 A1 | 10/2020 |

OTHER PUBLICATIONS

"Chemical and Biological Studies on New Cigarette Prototypes That Heat Instead of Burn Tobacco", R. J. Reynolds Tobacco Company, 1988.

International Search Report in the corresponding International Application No. PCT/IB2021/053552, dated Jun. 21, 2021, 6 pages.

* cited by examiner

AEROSOL DELIVERY DEVICE WITH SLIDING AND AXIALLY ROTATING LOCKING MECHANISM

FIELD OF THE DISCLOSURE

The present disclosure relates to aerosol delivery devices and systems, such as smoking articles; and more particularly, to aerosol delivery devices and systems that utilize heat sources, such as combustible carbon-based ignition sources, for the production of aerosol (e.g., smoking articles for purposes of yielding components of tobacco, tobacco extracts, nicotine, synthetic nicotine, non-nicotine flavoring, and other materials in an inhalable form, commonly referred to as heat-not-burn systems or electronic cigarettes). Components of such articles may be made or derived from tobacco, or those articles may be characterized as otherwise incorporating tobacco for human consumption, and which may be capable of vaporizing components of tobacco and/or other tobacco related materials to form an inhalable aerosol for human consumption.

BACKGROUND

Many smoking articles have been proposed through the years as improvements upon, or alternatives to, smoking products based upon combusting tobacco. Example alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Various manners and methods for assembling smoking articles that possess a plurality of sequentially arranged segmented components have been proposed. See, for example, the various types of assembly techniques and methodologies set forth in U.S. Pat. No. 5,469,871 to Barnes et al. and U.S. Pat. No. 7,647,932 to Crooks et al.; and U.S. Pat. App. Pub. Nos. 2010/0186757 to Crooks et al.; 2012/0042885 to Stone et al., and 2012/00673620 to Conner et al.; each of which is incorporated by reference herein in its entirety.

Certain types of cigarettes that employ carbonaceous fuel elements have been commercially marketed under the brand names "Premier," "Eclipse" and "Revo" by R. J. Reynolds Tobacco Company. See, for example, those types of cigarettes described in Chemical and Biological Studies on New Cigarette Prototypes that Heat Instead of Burn Tobacco, R. J. Reynolds Tobacco Company Monograph (1988) and Inhalation Toxicology, 12:5, p. 1-58 (2000). Additionally, a similar type of cigarette has been marketed in Japan by Japan Tobacco Inc. under the brand name "Steam Hot One."

In some instances, some smoking articles, particularly those that employ a traditional paper wrapping material, are also prone to scorching of the paper wrapping material overlying an ignitable fuel source, due to the high temperature attained by the fuel source in proximity to the paper wrapping material. This can reduce enjoyment of the smoking experience for some consumers and can mask or undesirably alter the flavors delivered to the consumer by the aerosol delivery components of the smoking articles. In further instances, traditional types of smoking articles can produce relatively significant levels of gasses, such as carbon monoxide and/or carbon dioxide, during use (e.g., as products of carbon combustion). In still further instances, traditional types of smoking articles may suffer from poor performance with respect to aerosolizing the aerosol forming component(s).

As such, it would be desirable to provide smoking articles that address one or more of the technical problems sometimes associated with traditional types of smoking articles. In particular, it would be desirable to provide a smoking article that is easy to use and that provides reusable and/or replaceable components.

BRIEF SUMMARY

In various implementations, the present disclosure relates to aerosol delivery devices and holders for use with removable and replaceable cartridges. The present disclosure includes, without limitation, the following example implementations:

A holder for use with a removable and replaceable substrate cartridge, the holder comprising a first body portion defining a main body and a guide post extending from the main body, the guide post defining a distal end, and the main body defining an opposite mouth end, the guide post further defining a receiving chamber extending at least a portion therethrough, and a second body portion, wherein the second body portion is configured to rotate about and slide along at least a portion of the guide post to and from at least a use position, wherein the second body portion is proximate the main body of the first body portion and the substrate cartridge is retained in the receiving chamber, and an open position, wherein the second body portion is rotated relative to and extended away from the main body of the first body portion such that the substrate cartridge can be inserted into or removed from the receiving chamber.

The holder of any preceding example implementation, or any combination of any preceding example implementations, wherein the guide post includes a guide slot, wherein the second body portion includes a guide pin, and wherein the guide pin is configured to move within the guide slot to and from the use position and the open position.

The holder of any preceding example implementation, or any combination of any preceding example implementations, wherein the guide post has a substantially cylindrical shape.

The holder of any preceding example implementation, or any combination of any preceding example implementations, wherein the second body portion is biased in the open position relative to the main body of the first body portion.

The holder of any preceding example implementation, or any combination of any preceding example implementations, wherein the second body portion includes a rotation limitation feature and the first body portion includes an extension slot.

The holder of any preceding example implementation, or any combination of any preceding example implementations, wherein the second body portion includes a pair of openings proximate a distal end thereof.

The holder of any preceding example implementation, or any combination of any preceding example implementations, wherein at least one of the first body portion or the second body portion includes a cartridge retention feature.

The holder of any preceding example implementation, or any combination of any preceding example implementations, wherein the cartridge retention feature comprises one or more retention spheres disposed in the guide post.

The holder of any preceding example implementation, or any combination of any preceding example implementations, wherein the cartridge retention feature further comprises one or more corresponding cam surfaces located on an inner surface of the second body portion.

The holder of any preceding example implementation, or any combination of any preceding example implementations, wherein at least one of first body portion or the second body portion has a substantially oblong overall shape.

An aerosol delivery device comprising a removable cartridge comprising a substrate portion that includes a substrate material having an aerosol precursor composition configured to form an aerosol upon application of heat thereto, and a holder comprising a first body portion defining a main body and a guide post extending from the main body, the guide post defining a distal end, and the main body defining an opposite mouth end, the guide post further defining a receiving chamber extending at least a portion therethrough, and a second body portion, wherein the second body portion is configured to rotate about and slide along at least a portion of the guide post to and from at least a use position, wherein the second body portion is proximate the main body of the first body portion and the cartridge is retained in the receiving chamber, and an open position, wherein the second body portion is rotated relative to and extended away from the main body of the first body portion such that the cartridge can be inserted into or removed from the receiving chamber.

The aerosol delivery device of any preceding example implementation, or any combination of any preceding example implementations, wherein the guide post includes a guide slot, wherein the second body portion includes a guide pin, and wherein the guide pin is configured to move within the guide slot to and from the use position and the open position.

The aerosol delivery device of any preceding example implementation, or any combination of any preceding example implementations, wherein the guide post has a substantially cylindrical shape.

The aerosol delivery device of any preceding example implementation, or any combination of any preceding example implementations, wherein the second body portion is biased in the open position relative to the main body of the first body portion.

The aerosol delivery device of any preceding example implementation, or any combination of any preceding example implementations, wherein the second body portion includes a rotation limitation feature and the first body portion includes an extension slot.

The aerosol delivery device of any preceding example implementation, or any combination of any preceding example implementations, wherein the second body portion includes a pair of openings proximate a distal end thereof, which are also configured to be proximate the heat source of the cartridge when in the use position.

The aerosol delivery device of any preceding example implementation, or any combination of any preceding example implementations, wherein at least one of the first body portion or the second body portion includes a cartridge retention feature.

The aerosol delivery device of any preceding example implementation, or any combination of any preceding example implementations, wherein the cartridge retention feature comprises one or more retention spheres disposed in the guide post.

The aerosol delivery device of any preceding example implementation, or any combination of any preceding example implementations, wherein the cartridge retention feature further comprises one or more corresponding cam surfaces located on an inner surface of the second body portion.

The aerosol delivery device of any preceding example implementation, or any combination of any preceding example implementations, wherein at least one of first body portion or the second body portion has a substantially oblong overall shape.

The aerosol delivery device of any preceding example implementation, or any combination of any preceding example implementations, wherein the cartridge further comprises a heat portion including a heat source configured to generate heat.

The aerosol delivery device of any preceding example implementation, or any combination of any preceding example implementations, wherein the substrate portion is disposed proximate the heat source.

A kit comprising at least one holder and at least one removable cartridge, wherein the at least one removable cartridge comprises a substrate portion that includes a substrate material having an aerosol precursor composition configured to form an aerosol upon application of heat thereto, and wherein the at least one holder comprises a first body portion defining a main body and a guide post extending from the main body, the guide post defining a distal end, and the main body defining an opposite mouth end, the guide post further defining a receiving chamber extending at least a portion therethrough, and a second body portion, wherein the second body portion is configured to rotate about and slide along at least a portion of the guide post to and from at least a use position, wherein the second body portion is proximate the main body of the first body portion and the cartridge is retained in the receiving chamber, and an open position, wherein the second body portion is rotated relative to and extended away from the main body of the first body portion such that the cartridge can be inserted into or removed from the receiving chamber.

The kit of any preceding example implementation, or any combination of any preceding example implementations, wherein the guide post includes a guide slot, wherein the second body portion includes a guide pin, and wherein the guide pin is configured to move within the guide slot to and from the use position and the open position.

The kit of any preceding example implementation, or any combination of any preceding example implementations, wherein the guide post has a substantially cylindrical shape.

The kit of any preceding example implementation, or any combination of any preceding example implementations, wherein the second body portion is biased in the open position relative to the main body of the first body portion.

The kit of any preceding example implementation, or any combination of any preceding example implementations, wherein the second body portion includes a rotation limitation feature and the first body portion includes an extension slot.

The kit of any preceding example implementation, or any combination of any preceding example implementations, wherein the second body portion includes a pair of openings proximate a distal end thereof, which are also configured to be proximate the heat source of the cartridge when in the use position.

The kit of any preceding example implementation, or any combination of any preceding example implementations, wherein at least one of the first body portion or the second body portion includes a cartridge retention feature.

The kit of any preceding example implementation, or any combination of any preceding example implementations, wherein the cartridge retention feature comprises one or more retention spheres disposed in the guide post.

The kit of any preceding example implementation, or any combination of any preceding example implementations, wherein the cartridge retention feature further comprises one or more corresponding cam surfaces located on an inner surface of the second body portion.

The kit of any preceding example implementation, or any combination of any preceding example implementations, wherein at least one of first body portion or the second body portion has a substantially oblong overall shape.

The kit of any preceding example implementation, or any combination of any preceding example implementations, wherein the cartridge further comprises a heat portion including a heat source configured to generate heat.

The kit of any preceding example implementation, or any combination of any preceding example implementations, wherein the substrate portion is disposed proximate the heat source.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

Figure 1:
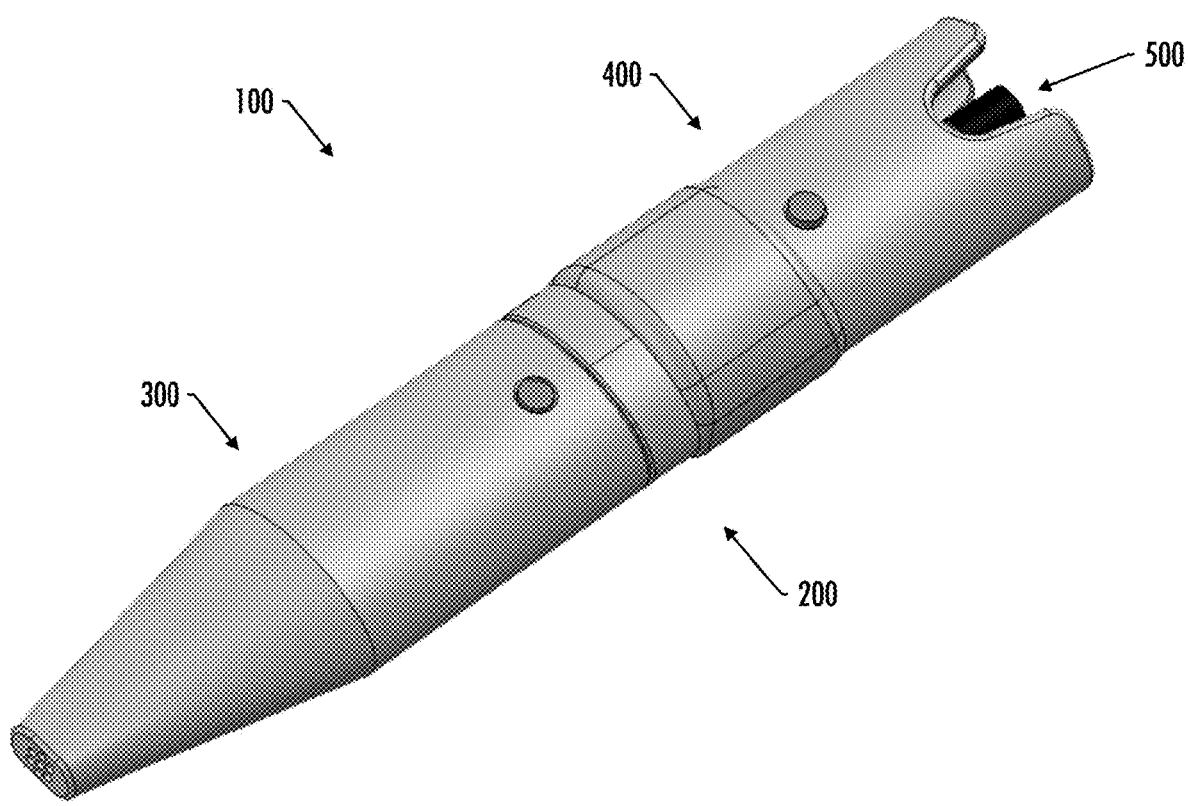
Figure 2A:
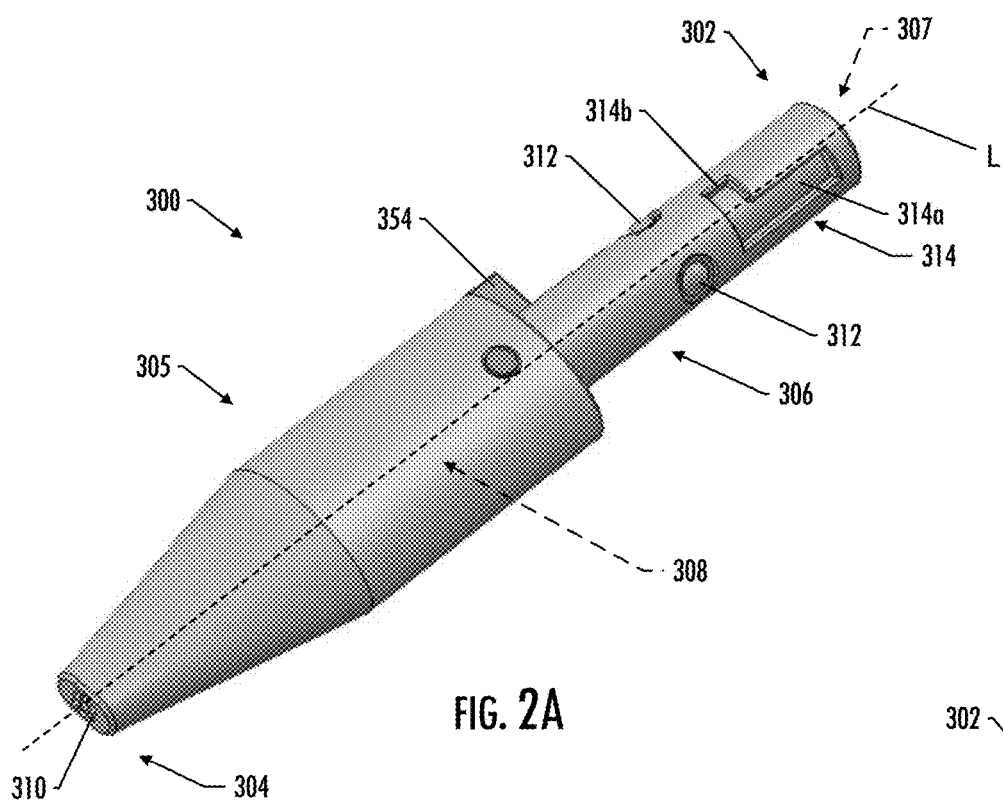
Figure 2B:
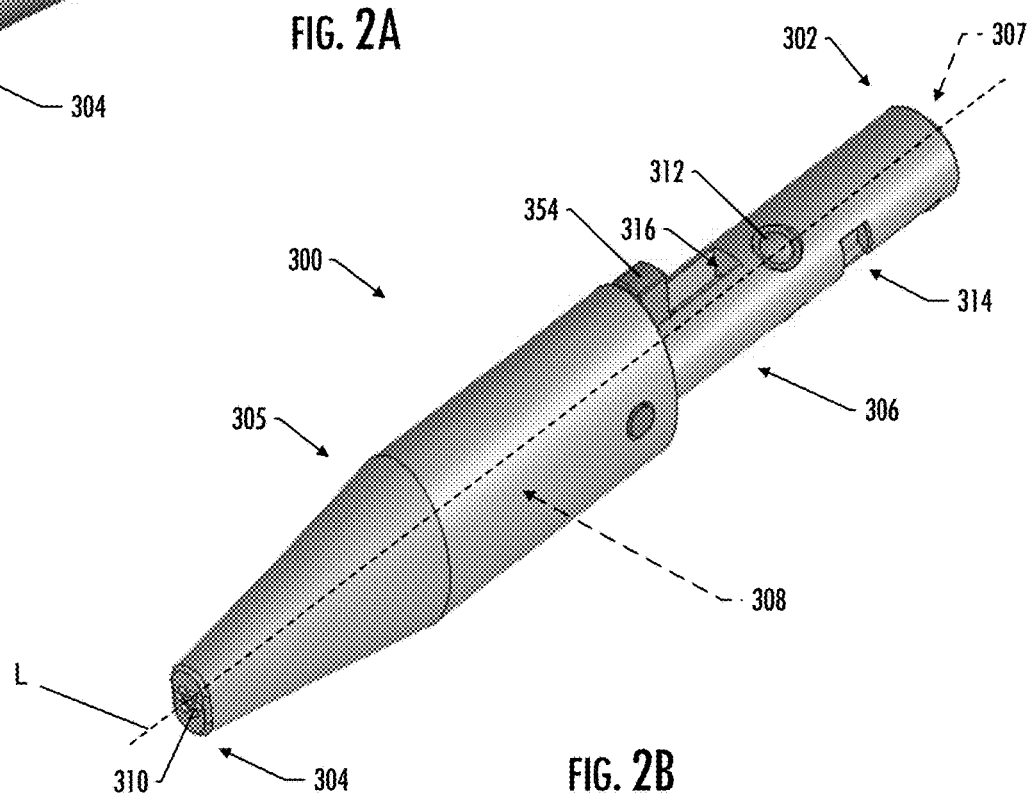
Figure 3A:
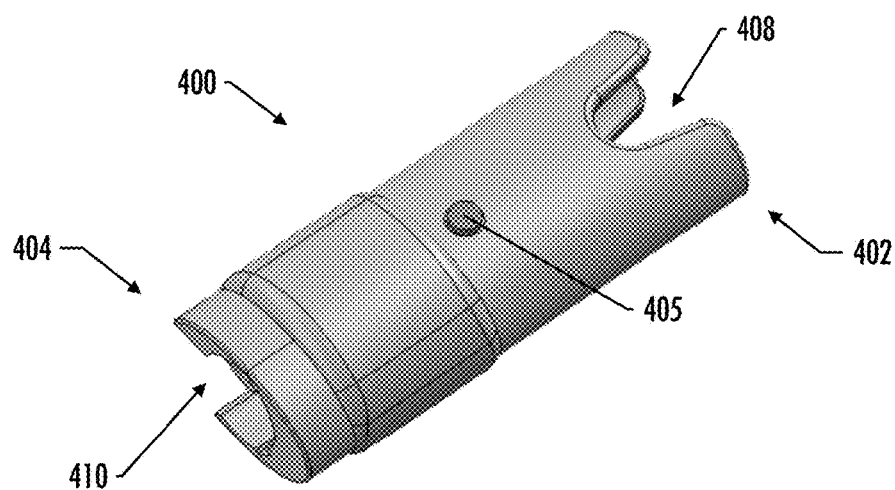
Figure 3B:
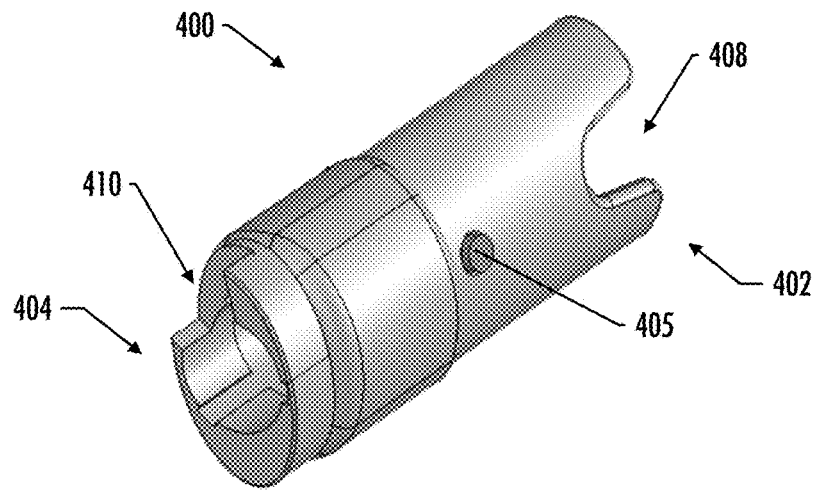
Figure 4:
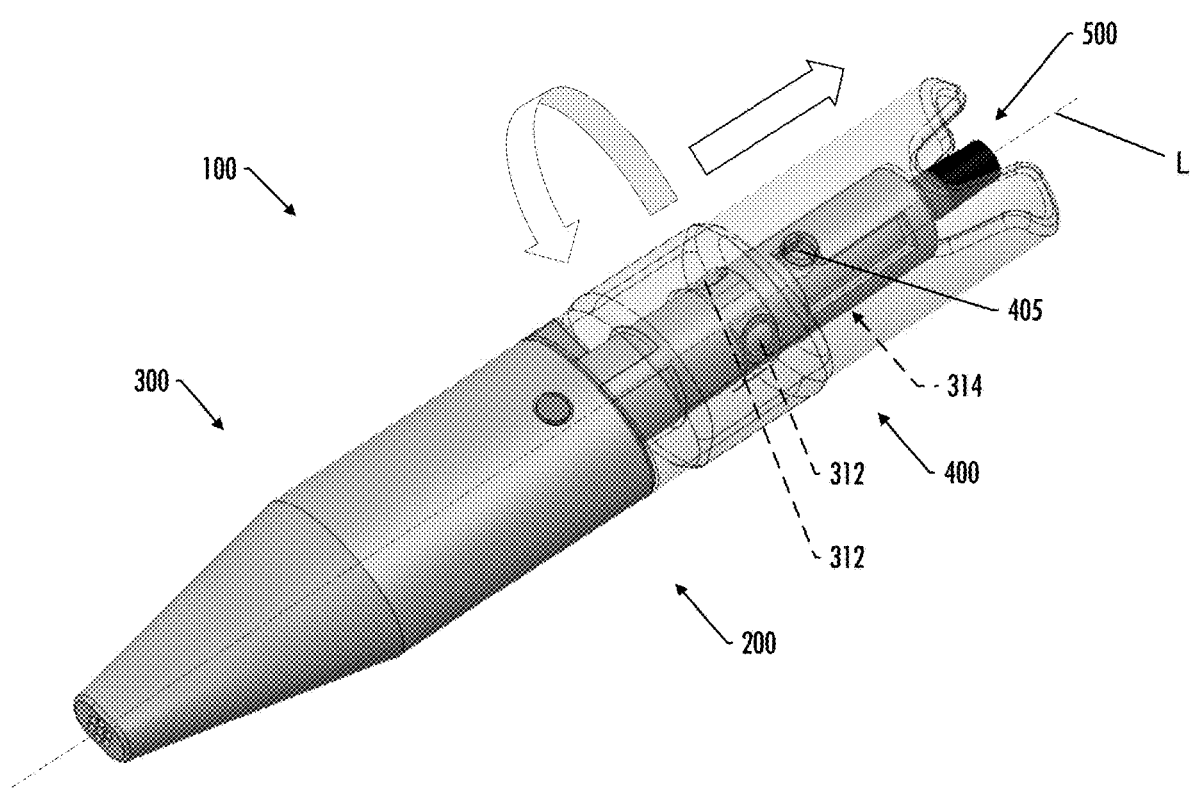
Figure 5:
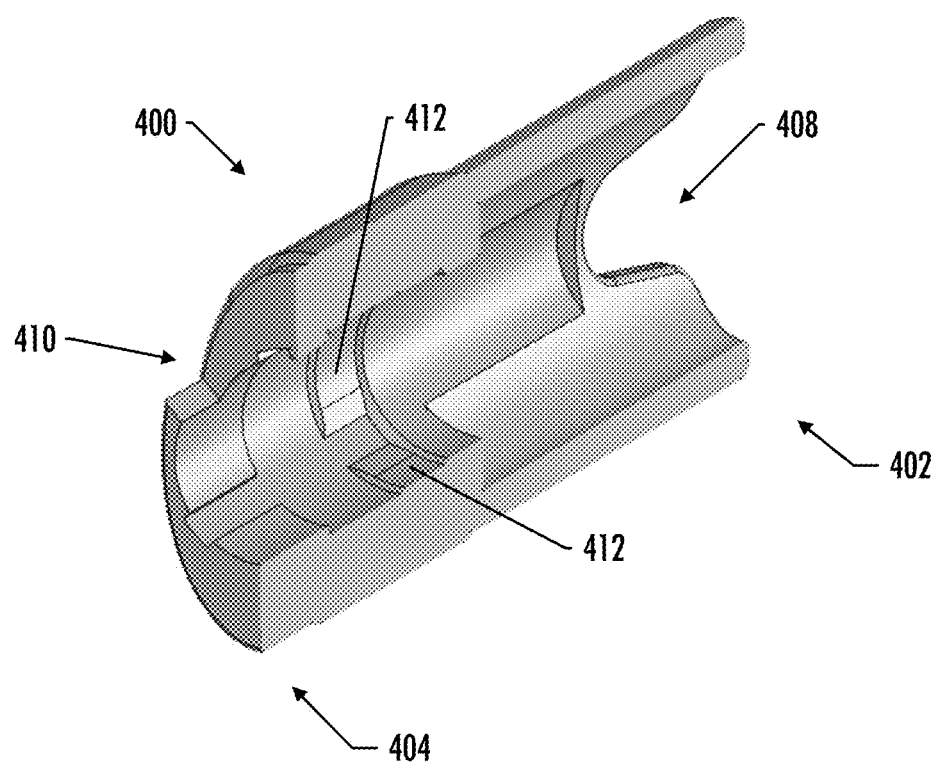
Figure 6A:
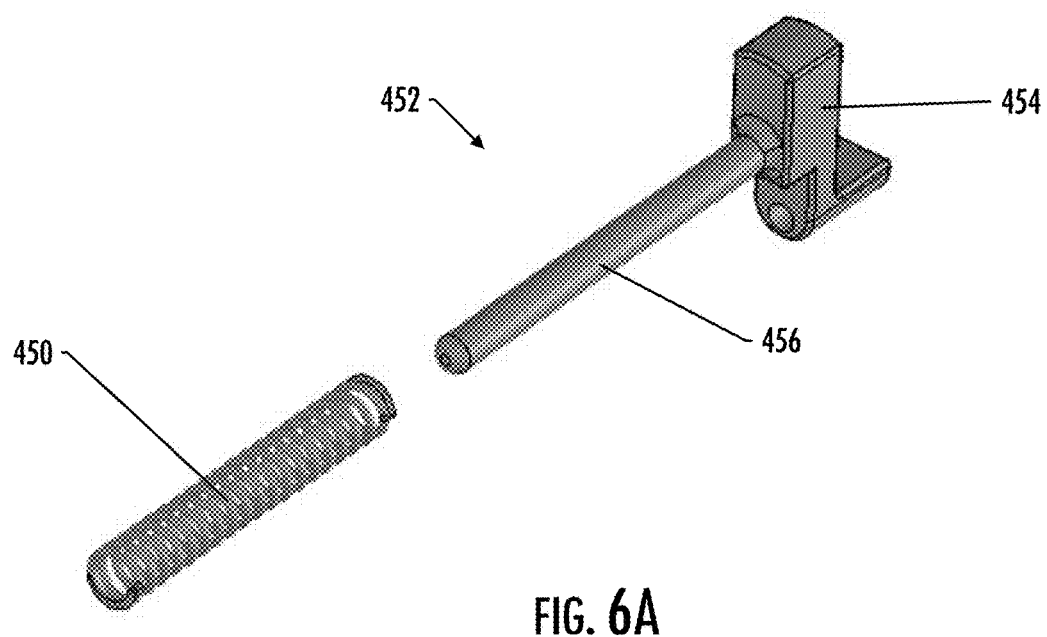
Figure 6B:
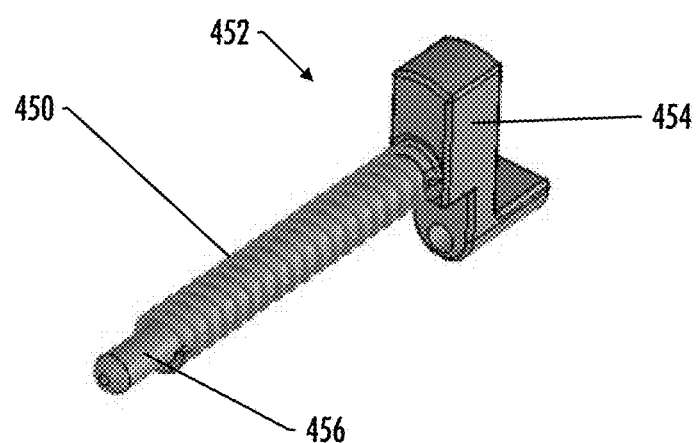
Figure 7:
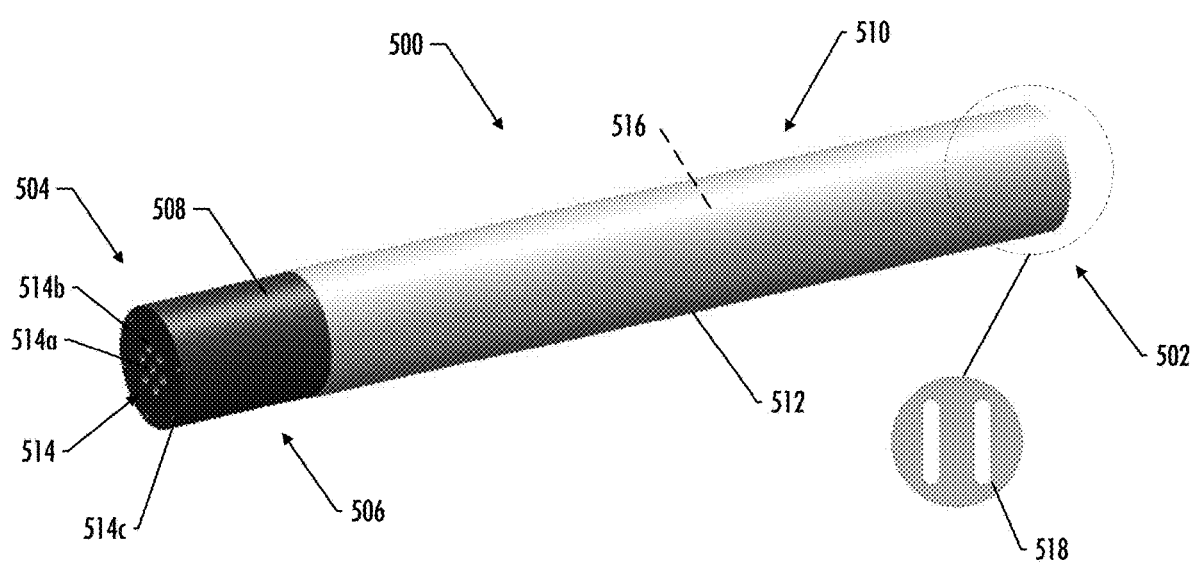
Figure 8:
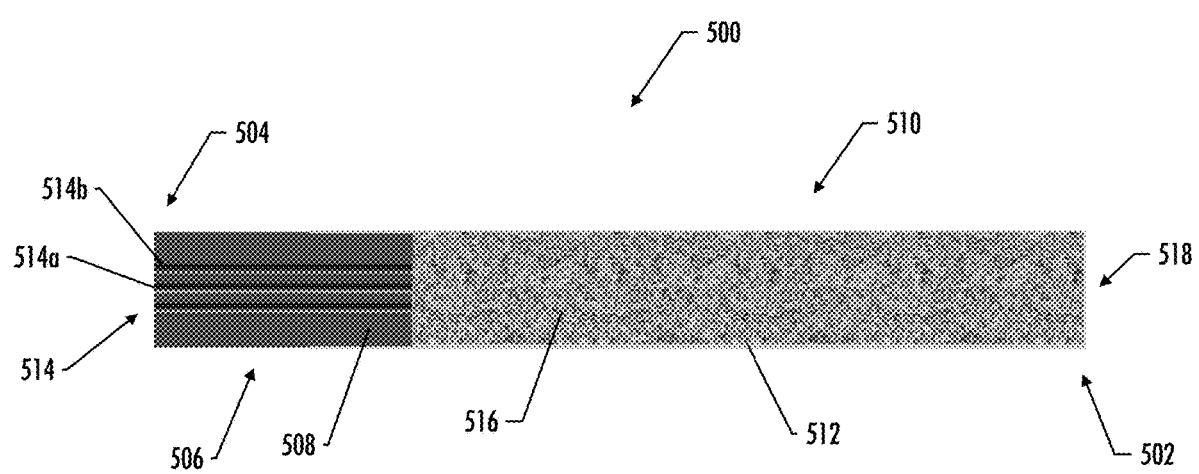

Having thus described the disclosure in the foregoing general terms, reference will now be made to the accompanying drawings, which are not necessarily drawn to scale, and wherein:

FIG. 1 illustrates a perspective view of an aerosol delivery device according to one implementation of the present disclosure;

FIG. 2A illustrates a perspective view of a first body portion of an aerosol delivery device, according to one implementation of the present disclosure;

FIG. 2B illustrates a perspective view of a first body portion of an aerosol delivery device, according to one implementation of the present disclosure;

FIG. 3A illustrates a perspective view of a second body portion of an aerosol delivery device, according to one implementation of the present disclosure;

FIG. 3B illustrates a perspective view of a second body portion of an aerosol delivery device, according to one implementation of the present disclosure;

FIG. 4 illustrates a perspective view of an aerosol delivery device, according to one implementation of the present disclosure;

FIG. 5 illustrates a perspective cross-section view of a second body portion of an aerosol delivery device, according to one implementation of the present disclosure;

FIG. 6A illustrates a rotation limitation and biasing feature of an aerosol delivery device, according to one implementation of the present disclosure;

FIG. 6B illustrates a rotation limitation and biasing feature of an aerosol delivery device, according to one implementation of the present disclosure;

FIG. 7 illustrates a perspective view of a removable and replaceable cartridge, according to one implementation of the present disclosure; and FIG. 8 illustrates a longitudinal cross-section view of a removable and replaceable cartridge, according to one implementation of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure is embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure provides descriptions of articles (and the assembly and/or manufacture thereof) in which a material is heated (preferably without combusting the material to any significant degree) to form an aerosol and/or an inhalable substance; such articles most preferably being sufficiently compact to be considered "hand-held" devices. In preferred aspects, the articles are characterized as smoking articles. As used herein, the term "smoking article" is intended to mean an article and/or device that provides many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article and/or device. As used herein, the term "smoking article" does not necessarily mean that, in operation, the article or device produces smoke in the sense of an aerosol resulting from by-products of combustion or pyrolysis of tobacco, but rather, that the article or device yields vapors (including vapors within aerosols that are considered to be visible aerosols that might be considered to be described as smoke-like) resulting from volatilization or vaporization of certain components, elements, and/or the like of the article and/or device. In preferred aspects, articles or devices characterized as smoking articles incorporate tobacco and/or components derived from tobacco.

As noted, aerosol generating components of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that component much like a smoker employs a traditional type of smoking article, draw on one end of that piece for inhalation of aerosol produced by that piece, take or draw puffs at selected intervals of time, and the like.

Articles or devices of the present disclosure are also characterized as being vapor-producing articles, aerosol delivery articles, or medicament delivery articles. Thus, such articles or devices are adaptable so as to provide one or more substances in an inhalable form or state. For example, inhalable substances are substantially in the form of a vapor (e.g., a substance that is in the gas phase at a temperature lower than its critical point). Alternatively, inhalable substances are in the form of an aerosol (e.g., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like. In some implementations, the terms "vapor" and "aerosol" may be interchangeable. Thus, for simplicity, the terms "vapor" and "aerosol" as used to describe the disclosure are understood to be interchangeable unless stated otherwise.

In use, smoking articles of the present disclosure are subjected to many of the physical actions of an individual in using a traditional type of smoking article (e.g., a cigarette, cigar, or pipe that is employed by lighting with a flame and used by inhaling tobacco that is subsequently burned and/or combusted). For example, the user of a smoking article of the present disclosure holds that article much like a traditional type of smoking article, draws on one end of that article for inhalation of an aerosol produced by that article, and takes puffs at selected intervals of time.

While the systems are generally described herein in terms of implementations associated with smoking articles such as so-called "tobacco heating products," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Smoking articles of the present disclosure generally include a number of elements provided or contained within an enclosure of some sort, such as a housing, an outer wrap, or wrapping, a casing, a component, a module, a member, or the like. The overall design of the enclosure is variable, and the format or configuration of the enclosure that defines the overall size and shape of the smoking article is also variable. It is desirable, in some aspects, that the overall design, size, and/or shape of the enclosure resembles that of a conventional cigarette or cigar. Typically, an enclosure resembling the shape of a cigarette or cigar comprises separable components, members, or the like that are engaged to form the enclosure. For example, such a smoking article may comprise, in some aspects, separable components that include a holder and a cartridge that includes an aerosol delivery component (such as, for example, a substrate material) and a heat source component. In various aspects, the heat source may be capable of generating heat to aerosolize a substrate material that comprises, for example, an extruded structure and/or substrate, a substrate material associated with an aerosol precursor composition, tobacco and/or a tobacco related material, such as a material that is found naturally in tobacco that is isolated directly from the tobacco or synthetically prepared, in a solid or liquid form (e.g., beads, sheets, shreds, a wrap), or the like. In some implementations, an extruded structure may comprise tobacco products or a composite of tobacco with other materials such as, for example, ceramic powder. In other implementations, a tobacco extract/slurry may be loaded into porous ceramic beads. Other implementations may use non-tobacco products. In some implementations aerosol precursor composition-loaded porous beads/powders (ceramics) may be used. In other implementations, rods/cylinders made of extruded slurry of ceramic powder and aerosol precursor composition may be used.

According to certain aspects of the present disclosure, it may be advantageous to provide an aerosol delivery device that is easy to use and that provides reusable and/or replaceable components. FIG. 1 illustrates such a device. In particular, FIG. 1 illustrates a perspective view of an aerosol delivery device 100, according to an example implementation of the present disclosure.

As shown in the figure, the aerosol delivery device 100 of the depicted implementation includes a holder 200 comprising a first body portion 300 and a second body portion 400, and removable and replaceable cartridge 500 (described in more detail below with respect to FIGS. 7 and 8). In the depicted implementation, the holder 200 (including the first body portion 300 and the second body portion 400) has a substantially oblong overall shape; however, in other implementations the holder or any of its components may have a different shape. For example, in some implementations the holder (and/or any of its components) may have a substantially cylindrical shape that imitates the shape of a traditional cigarette. In other implementations the holder (and/or any of its components) may have a substantially rectangular shape, such as a substantially rectangular cuboid shape. In other implementations, the holder (and/or any of its components) may have other hand-held shapes. For example, in some implementations the holder (and/or any of its components) may have a small box shape, various pod mod shapes, or a fob-shape.

As best shown in FIGS. 2A and 2B, which illustrate perspective views of the first body portion 300 of the aerosol delivery device 100 of FIG. 1, the first body portion 300 defines a distal end 302 and an opposite mouth end 304, and a longitudinal axis L extending therethrough. In the depicted implementation, the first body portion 300 further defines a main body 305 and a guide post 306 that extends from the end of the main body 305 to the distal end 302 of the first body portion 300. In the depicted implementation, the guide post 306 further defines a receiving chamber 307 that begins at the distal end 302 of the guide post 306 and extends at least a portion therethrough. In the depicted implementation, the main body 305 tapers toward the mouth end 304, however, in other implementations the first body portion may have a substantially consistent shape at the mouth end.

As will be described in more detail below, the second body portion 400 of the depicted implementation is configured to rotate about and slide along the guide post 306. In the depicted implementation, the guide post 306 has a substantially cylindrical shape and extends less than half the total length of the first body portion 300. In other implementations, however, the guide post may have a different shape (e.g., a non-cylindrical shape) and may extend more or less than that length. Although other dimensions are possible, the guide post 306 of the depicted implementation has an outer diameter that is less than an outer width of the first body portion 300. In the depicted implementation, an aerosol passage 308 is defined through the first body portion 300, extending from the distal end 302, through the guide post 306 and the main body 305 of the first body portion 300, and through the mouth end 304. In the depicted implementation, the mouth end 304 of the first body portion 300 includes a plurality of clustered substantially circular openings 310 extending therethrough. In other implementations, however, there may be a single opening having the same shape or a different shape, or a plurality of openings each having different shapes.

In various implementations, the first body portion and/or the second body portion may be made of moldable plastic materials such as, for example, polycarbonate, polyethylene, acrylonitrile butadiene styrene (ABS), polyamide (Nylon), or polypropylene. In other implementations, however, the first body portion and/or the second body portion may be made of a different material, such as, for example, a different plastic material, a metal material (such as, but not limited to, stainless steel, aluminum, brass, copper, silver, gold, or bronze), a graphite material, a glass material, a ceramic material, a natural material (such as, but not limited to, a wood material), a composite material, or any combinations thereof. In the depicted implementation, the guide post 306 is part of the first body portion 300. In other implementations, however, the guide post may comprise a separate part and may be made of the same material or a different material than the first body portion or the second body portion.

In the depicted implementation, the first body portion 300 further includes a guide slot 314 that, as will be described in more detail below, is configured to facilitate movement of the second body portion 400 to and from an open position, wherein the cartridge 500 can be inserted into or removed from the receiving chamber, and a use position, wherein the cartridge 500 is retained in the receiving chamber. In the depicted implementation, the guide slot 314 is generally L-shaped with a longitudinal leg 314a of the slot 314 being substantially aligned with the longitudinal axis L of the first body portion 300, and a transverse leg 314b being substantially perpendicular to the longitudinal leg 314a. As will be described in more detail below, in such a manner the guide slot 314 may facilitate a rotating and sliding motion of the second body portion 400 relative to the first body portion 300. It should be noted that in other implementations, the guide slot may have other configurations that facilitate a rotating and sliding motion of the second body portion. For example, it some implementations the guide slot may have a curved configuration, such as, but not limited to, a spiral configuration or a partial spiral configuration.

In the depicted implementation, the guide post 306 includes a plurality of retention spheres 312, which form part of a cartridge retention feature (the other part of which is located in the second body portion 400, as will be described in more detail below). In the depicted implementation, there are three retention spheres 312 that are substantially equally spaced around the guide post 306 and that extend (at least in the use position) at least a portion therethrough into the receiving chamber 307. In other implementations, there may be more or less spheres. In still other implementations, the cartridge retention feature may have other configurations. For example, in some implementations the retention feature may comprise one or more resilient members. In other implementations, the outer housing of the cartridge and/or the holder may include one or more protrusions and/or spring features and corresponding detent features configured to retain the cartridge in the receiving chamber in the use position. In other implementations, the inner surface of the receiving chamber may have a decreasing diameter, and/or one or more portions having a decreased diameter, that may be configured to retain the cartridge in the receiving chamber in the use position. In other implementations, the holder may include retractable features configured to engage the cartridge to retain it in the receiving chamber in the use position. In other implementations, the holder may include one or more wedge features configured to engage and retain the cartridge in the receiving chamber in the use position. In still other implementations, one or more features of the cartridge and/or one or more features of the holder may create a releasable connection between the receiving chamber and the cartridge. For example, in some implementations the cartridge and the receiving chamber may have a releasable screw-type connection. In still other implementations, the cartridge may be retained in the receiving chamber via magnetic force. For example, in some implementations the outer housing of the cartridge may be made of a ferromagnetic material, and the receiving chamber may include one or more magnets. As such, although in the depicted implementation a portion of the cartridge retention feature is located in the first body portion and a portion of the cartridge retention feature is located in the second body portion, in other implementations the cartridge retention feature may be solely located in the first body portion and of the second body portion.

In various implementations, the retention spheres may be made of moldable plastic materials such as, for example, polycarbonate, polyethylene, acrylonitrile butadiene styrene (ABS), polyamide (Nylon), or polypropylene. In other implementations, however, the retention spheres may be made of a different material, such as, for example, a different plastic material, a metal material (such as, but not limited to, stainless steel, aluminum, brass, copper, silver, gold, or bronze), a graphite material, a glass material, a ceramic material, a natural material (such as, but not limited to, a wood material), a composite material, or any combinations thereof. In the depicted implementation, the retention spheres 312 are made of a metal material.

FIGS. 3A and 3B illustrate perspective views of the second body portion 400 of the aerosol delivery device 100 of FIG. 1. As shown in the figures, the second body portion 400 defines a distal end 402 and a near end 404, both of which are open. The second body portion 400 of the depicted implementation is configured to be positioned around the guide post 306 of the first body portion 300 such that it may move relative thereto. The distal end 402 of the second body portion 400 of the depicted implementation also includes a pair of opposing U-shaped openings 408, which are configured, when the cartridge 500 is inserted in the holder 200, to be located proximate the heat source of the cartridge 500. In the depicted implementation, the second body portion 400 has an oblong overall shape that substantially matches the oblong shape of the first body portion 300, however, as noted, in other implementations one or both the first body portion or the second body portion may have a different shape.

In the depicted implementation the second body portion 400 also includes a guide pin 405, which is configured to move within the guide slot 314 (see FIGS. 2A and 2B) of the first body portion 300. As noted above, the guide slot 314 is configured to facilitate rotation and sliding of the second body portion 400 relative to the first body portion 300. Such rotation and sliding of the second body portion 400 occurs when moving the second portion 400 to and from the use position and the open position. In particular, in the use position the near end 404 of the second body portion 400 is positioned proximate the main body 305 of the first body portion 300, and the guide pin 405 of the second body portion 400 is positioned proximate the terminal end of the transverse leg 314*b* of the guide slot 314 of the first body portion 300. In the open position, the second body portion 400 is rotated (in the depicted implementation approximately 45 degrees) relative to the first body portion 300, the near end 404 of the second body portion 400 is extended away from the main body 305 of the first body portion 300, and the guide pin 405 is located proximate the terminal end of the longitudinal leg 314*a* of the guide slot 314. It should be noted that in the open position of other implementations, the second body portion may be rotated more than or less than 45 degrees with respect to the first body portion.

Rotation and sliding movements of the second body portion 400 from the use position are shown in FIG. 4. For ease of illustration, the second body portion 400 of the holder 200 is shown as transparent. To move the second body portion 400 from the use position to the open position, the second body portion 400 is rotated clockwise (or counter clockwise based on the orientation of the guide slot) relative to the first body portion 300. This motion moves the guide pin 405 of the second body portion along the transverse leg 314*b* of the guide slot 314 of the first body portion 300. When the guide pin 405 reaches the end of the transverse leg 314*b* of the guide slot 314, the guide pin 405 then moves along the longitudinal leg 314*a* and away from the main body 305 of the first body portion 300, until it is positioned proximate the terminal end of the longitudinal leg 314*a*.

In the depicted implementation, the second body portion 400 is configured to be biased into the open position. In the depicted implementation, this occurs with the aid of a spring member 450, which is depicted in FIGS. 6A and 6B. In some implementations, rotation of the second body portion 400 relative to the first body portion 300 may be limited by a rotation limitation feature 452, which is also depicted in FIGS. 6A and 6B. In the depicted implementation, the rotation limitation feature 452 comprises a flange 454 and a post 456, which extends from the flange 454. In the depicted implementation, the second body portion 400 includes a rotation slot 410 (see FIGS. 3A and 3B), and the guide post 306 includes an extension slot 316 (see FIG. 2B). In some implementations, rotation of the second body portion may be limited (alternatively or additionally) by the flange of the rotation limitation feature and the rotation slot of the second body portion, and extension of the second body portion may be limited (alternatively or additionally) by the flange of the rotation limitation feature and the extension slot of the first body portion.

While in some implementations biasing and rotation limitation features may be provided separately, and other implementations need not include these features, in the depicted implementation the spring member 450 is configured to extend around the post 456 of the rotation limitation feature 452. In the depicted implementation, one end of the spring member 450 is positioned in a pocket of the first body portion 300 and the other end is positioned against the flange 454 of the rotation limitation feature 452. In such a manner, the spring member 450 of the depicted implementation is in a compressed state when the second body portion 400 is the use position, and an extended state (partially or fully) when the second body portion 400 is in an open position. In the extended state, one end of the spring remains anchored in the corresponding pocket of the first body portion 300, and the other end of the spring member 450 pushes against the flange 454 and thus the second body portion 400 until the guide pin 405 reaches the terminal end of the longitudinal leg 314*a* of the guide slot 314 (and/or the flange 454 reaches the end of the extension slot 316).

In various implementations, the rotation limitation feature may be made of moldable plastic materials such as, for example, polycarbonate, polyethylene, acrylonitrile butadiene styrene (ABS), polyamide (Nylon), or polypropylene. In other implementations, however, the rotation limitation feature may be made of a different material, such as, for example, a different plastic material, a metal material (such as, but not limited to, stainless steel, aluminum, brass, copper, silver, gold, or bronze), a graphite material, a glass material, a ceramic material, a natural material (such as, but not limited to, a wood material), a composite material, or any combinations thereof. In the depicted implementation, the rotation limitation feature 452 is a separate part from the spring member 450, and may be made of the same material or a different material (e.g., in one implementation the plunger may be made of a metal material, and the spring member may be made of a metal material). In other implementations, however, the spring member may be part of the rotation limitation feature.

The holder 200 of the depicted implementation is configured such that in the open position, the removable and replaceable cartridge 500 may be inserted into or removed from the cartridge receiving chamber 307, and in the use position the removable and replacement cartridge 500 may be retained in the cartridge receiving chamber 307. Although in various implementations retention of the cartridge may be accomplished in variety of different ways, in the depicted implementation this is accomplished via a cartridge retention feature that comprises one or more spheres 312 of the first body portion 300 (as noted above) and one or more cam surfaces 412 located on an inner wall of the second body portion. FIG. 5 illustrates a perspective cross-section view of the second body portion 400 of the aerosol delivery device 100 of FIG. 1. As shown in the figure, an inner wall of the second body portion 400 includes a plurality of cam surfaces 412, each of which extends inward toward the center of the second body portion 400. When in the use position, the cam surfaces 412 of the second body portion 400 are longitudinally aligned with the plurality of retention spheres 312 of the first body portion 300. In the depicted implementation, the first body portion 300 includes three retention spheres 312 and a corresponding number of cam surfaces 412. In other implementations, however, there may be more or less cam surfaces, and the number of cam surfaces need not equal the number of retention spheres.

As noted above, the retention spheres 312 are positioned around and extend through the guide post 306 of the first body portion 300, and (at least in the use position) into the receiving chamber 307. In the depicted implementation, the retention spheres 312 are configured to move inward and outward between an engaging position, in which the retention spheres 312 engage and substantially retain an outer surface the cartridge 500, and a non-engaged position in which the cartridge 500 is not retained by the retention spheres 312. These two positions correspond to the use position of the holder 200 and the open position of the holder 200, respectively. Although in some implementations the retention spheres may not be biased or may be biased in other positions, in the depicted implementation, the retention spheres 312 are biased into the non-engaged position. In various implementations, the retention spheres may be biased in variety of different ways, for example, by using spring elements, resilient materials, etc. Referring to FIG. 5, when the second body portion 400 of the depicted implementation is in the use position, the cam surfaces 412 of the second body portion 400 contact the retention spheres 312 positioning them in the engaging position, which is inward into the receiving chamber 307. When the second body portion 400 of the depicted implementation is in the open position, the retention spheres 312 move outward into the non-engaging position.

It should be noted that in some implementations, when device is in the use position and the cartridge is received in the retention feature, a draw by a user may cause air to flow through the cartridge for delivery to the user. In some implementations, air may enter the cartridge through the heat portion. In other implementations (such as, for example, implementations in which the cartridge includes a nonporous barrier between the heat portion and the substrate material), air may enter the cartridge at some area downstream from the heat portion. In still other implementations, a portion of air may enter the cartridge through the heat portion and a portion of air may enter the cartridge at some area downstream from the heat portion. In some implementations, the first body portion and/or the second body portion may include one or more airflow passageways that substantially align with one or more airflow intake openings located downstream from the heat portion and that extend through the outer housing of the cartridge. For example, in some implementations the guide post may include one or more airflow passageways that substantially align with one or more airflow intake openings of the cartridge.

FIG. 7 illustrates a perspective view of the removable and replaceable cartridge 500, according to an example implementation of the present disclosure. In the depicted implementation, the cartridge 500 defines a first end 502 and a distal end 504. The cartridge 500 of the depicted implementation further includes a heat portion 506 comprising a heat source 508, a substrate portion 510 comprising a substrate material 516 (see FIG. 8), and an outer housing 512 configured to circumscribe at least a portion of the heat source 508 and substrate material 516. It should be noted that although in the depicted implementation the cartridge 500 has a substantially cylindrical overall shape, in various other implementations, the cartridge or any of its components may have a different shape. For example, in some implementations the cartridge (and/or any of its components) may have a substantially rectangular shape, such as a substantially rectangular cuboid shape. In other implementations, the cartridge (and/or any of its components) may have other hand-held shapes. Some examples of cartridge configurations that may be applicable to the present disclosure can be found in U.S. patent application Ser. No. 16/515,637, filed on Jul. 18, 2019, and titled Aerosol Delivery Device with Consumable Cartridge, which is incorporated herein by reference in its entirety.

In some implementations a barrier may exist between the heat source and the substrate material. In some implementations, such a barrier may comprise a disc that may include one or more apertures therethrough. In some implementations, the barrier may be constructed of a metal material (such as, for example, stainless steel, aluminum, brass, copper, silver, gold, and bronze), or a graphite material, or a ceramic material, or a plastic material, or any combinations thereof. In some implementations, a heat transfer component, which may or may not comprise a barrier, may exist between the heat source and the substrate material. Some examples of heat transfer components are described in U.S. patent application Ser. No. 15/923,735, filed on Mar. 16, 2018, and titled Smoking Article with Heat Transfer Component, which is incorporated herein by reference in its entirety. In some implementations, a barrier and/or a heat transfer component may prevent or inhibit combustion gasses from being drawn through the substrate material (and/or from being drawn through air passageways through which aerosol is drawn).

In various implementations, the heat source may be configured to generate heat upon ignition thereof. In the depicted implementation, the heat source 508 comprises a combustible fuel element that has a generally cylindrical shape and that incorporates a combustible carbonaceous material. In other implementations, the heat source may have a different shape, for example, a prism shape having a cubic or hexagonal cross-section. Carbonaceous materials generally have a high carbon content. Some carbonaceous materials may be composed predominately of carbon, and/or typically have carbon contents of greater than about 60 percent, generally greater than about 70 percent, often greater than about 80 percent, and frequently greater than about 90 percent, on a dry weight basis.

In some instances, the heat source may incorporate elements other than combustible carbonaceous materials (e.g., tobacco components, such as powdered tobaccos or tobacco extracts; flavoring agents; salts, such as sodium chloride, potassium chloride and sodium carbonate; heat stable graphite a hollow cylindrical (e.g., tube) fibers; iron oxide powder; glass filaments; powdered calcium carbonate; alumina granules; ammonia sources, such as ammonia salts; and/or binding agents, such as guar gum, ammonium alginate and sodium alginate). In other implementations, the heat source may comprise a plurality of ignitable objects, such as, for example, a plurality of ignitable beads. It should be noted that in other implementations, the heat source may differ in composition or relative content amounts from those listed above. For example, in some implementations different forms of carbon could be used as a heat source, such as graphite or graphene. In other implementations, the heat source may have increased levels of activated carbon, different porosities of carbon, different amounts of carbon, blends of any above mentioned components, etc. In still other implementations, the heat source may comprise a non-carbon heat source, such as, for example, a combustible liquefied gas configured to generate heat upon ignition thereof. For example, in some implementations, the liquefied gas may comprise one or more of petroleum gas (LPG or LP-gas), propane, propylene, butylenes, butane, isobutene, methyl propane, or n-butane. In still other implementations, the heat source may comprise a chemical reaction based heat source, wherein ignition of the heat source comprises the interaction of two or more individual components. For example, a chemical reaction based heat source may comprise metallic agents and an activating solution, wherein the heat source is activated when the metallic agents and the activating solution come in contact. Some examples of chemical based heat sources can be found in U.S. Pat. No. 7,290,549 to Banerjee et al., which is incorporated herein by reference in its entirety. Combinations of heat sources are also possible. Although specific dimensions of an applicable heat source may vary, in the depicted implementation, the heat source 508 has a length in an inclusive range of approximately 5 mm to approximately 20 mm, and in some implementations may be approximately 12 mm, and an overall diameter in an inclusive range of approximately 3 mm to approximately 8 mm, and in some implementations may be approximately 4.8 mm (and in some implementations, approximately 7 mm).

Although in other implementations, the heat source may be constructed in a variety of ways, in the depicted implementation, the heat source 508 is extruded or compounded using a ground or powdered carbonaceous material, and has a density that is greater than about 0.5 g/cm$^3$, often greater than about 0.7 g/cm$^3$, and frequently greater than about 1 g/cm$^3$, on a dry weight basis. See, for example, the types of fuel source components, formulations and designs set forth in U.S. Pat. No. 5,551,451 to Riggs et al. and U.S. Pat. No. 7,836,897 to Borschke et al., which are incorporated herein by reference in their entireties.

Although in various implementations the heat source may have a variety of forms, including, for example, a substantially solid cylindrical shape or a hollow cylindrical (e.g., tube) shape, the heat source 508 of the depicted implementation comprises an extruded monolithic carbonaceous material that has a generally cylindrical shape that includes a plurality of internal passages 514 extending longitudinally from a first end of the heat source 508 to an opposing second end of the heat source 508. In the depicted implementation there are approximately thirteen internal passages 514 comprising a single central internal passage 514a, six surrounding internal passages 514b, which are spaced from the central internal passages 514a and have a similar size (e.g., diameter) to that of the central internal passage 514a, and six peripheral internal passages 514c, which are spaced from an outer surface of the heat source 508 and are smaller in diameter than that of the central internal passage 514a. It should be noted that in other implementations, there need not be a plurality of internal passages and/or the plurality of internal passages may take other forms and/or sizes. For example, in some implementations, there may be as few as two internal passages, and still other implementations may include as few as a single internal passage. Still other implementations may include no internal passages at all. Additional implementations may include multiple internal passages that may be of unequal diameter and/or shape and which may be unequally spaced and/or located within the heat source.

Some implementations may alternatively, or additionally include one or more peripheral grooves that extend longitudinally from a first end of the heat source to an opposing second end, although in other implementations the grooves need not extend the full length of the heat source. In some implementations, such grooves may be substantially equal in width and depth and may be substantially equally distributed about a circumference of the heat source. In such implementations, there may be as few as two grooves, and still other implementations may include as few as a single groove. Still other implementations may include no grooves at all. Additional implementations may include multiple grooves that may be of unequal width and/or depth, and which may be unequally spaced around a circumference of the heat source. In still other implementations, the heat source may include flutes and/or slits extending longitudinally from a first end of the extruded monolithic carbonaceous material to an opposing second end thereof. In some implementations, the heat source may comprise a foamed carbon monolith formed in a foam process of the type disclosed in U.S. Pat. No. 7,615,184 to Lobovsky, which is incorporated herein by reference in its entirety. As such, some implementations may provide advantages with regard to reduced time taken to ignite the heat source. In some other implementations, the heat source may be co-extruded with a layer of insulation (not shown), thereby reducing manufacturing time and expense. Other implementations of fuel elements include carbon fibers of the type described in U.S. Pat. No. 4,922,901 to Brooks et al. or other heat source implementations such as is disclosed in U.S. Pat. App. Pub. No. 2009/0044818 to Takeuchi et al., each of which is incorporated herein by reference in its entirety. Further examples of heat sources including debossed heat source systems, methods, and smoking articles that include such heat sources are disclosed in U.S. patent application Ser. No. 15/902,665, filed on Feb. 22, 2018, and titled System for Debossing a Heat Generation Member, a Smoking Article Including the Debossed Heat Generation Member, and a Related Method, which is incorporated herein by reference in its entirety.

Generally, the heat source is positioned sufficiently near an aerosol delivery component (e.g., the substrate portion) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate component, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various smoking article elements are appreciated upon consideration of commercially available electronic smoking articles, such as those representative products listed in the background art section of the present disclosure.

FIG. 8 illustrates a longitudinal cross-section view of the cartridge 500 of FIG. 7. As shown in the figure, the substrate material 516 of the depicted implementation has opposed first and second ends, with the heat source 508 disposed adjacent the first end of the substrate material 516. Although dimensions of the various components of the cartridge may vary due to the needs of a particular application, in the depicted implementation the cartridge 500 may have an overall length in an inclusive range of approximately 10 mm to approximately 50 mm and a diameter in an inclusive range of approximately 2 mm to approximately 20 mm. In addition, in the depicted implementation the outer housing 312 may have a thickness in the inclusive range of approximately 0.05 mm to 0.5 mm. Furthermore, in the depicted implementation the substrate portion 510 may have a length in the inclusive range of approximately 5 mm to 30 mm and a diameter slightly less than that of the overall cartridge in order to accommodate the thickness of the housing 512, such as, for example, a diameter in an inclusive range of approximately 2.9 mm to approximately 9.9 mm. In the depicted implementation, the substrate material 516 comprises tobacco beads, which may have diameter sizes in range of approximately 0.5 mm to 2.0 mm, although in other implementations the size may differ. In other implementations, the substrate material may be a granulated tobacco material or cut filler tobacco. Although other implementations may differ, in the depicted implementation the outer housing 512 of the cartridge 500 is filled to about 80-90% capacity to allow for insertion of the heat source 508.

In the depicted implementation, the substrate portion 510 comprises a substrate material 516 having a single segment, although in other implementations the substrate portion may include one or more additional substrate material segments. For example, in some implementations, the aerosol delivery device may further comprise a second substrate material segment (not shown) having opposed first and second ends. In various implementations, one or more of the substrate materials may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Other possible compositions, components, and/or additives for use in a substrate material (and/or substrate materials) are described in more detail below. It should be noted that the subsequent discussion should be applicable any substrate material usable in the smoking articles described herein (such as, for example, the substrate material 516 of the depicted implementation).

In the depicted implementation, ignition of the heat source 508 results in aerosolization of the aerosol precursor composition associated with the substrate material 516. In various implementations, the aerosol passage 308 is configured to receive the generated aerosol therethrough in response to a draw applied to the mouth end 304 of the first body portion 300 by a user. In some implementations the mouth end 304, or other portion of the first body portion 300 may include a filter configured to receive the aerosol therethrough in response to the draw applied to the mouth end 304 of the first body portion. In various implementations, the filter may be provided, in some aspects, as a circular disc radially and/or longitudinally disposed proximate the end of the holder opposite the receiving end. In this manner, upon a draw on the mouth end 304 of the first body portion 300, the filter may receive the aerosol flowing through holder 200 of the aerosol delivery device 100. In some implementations, the filter may comprise discrete segments. For example, some implementations may include a segment providing filtering, a segment providing draw resistance, a hollow segment providing a space for the aerosol to cool, other filter segments, and any one or any combination of the above. In some implementations, the mouthpiece may include a filter that may also provide a flavorant additive. In some implementations, a filter may include one or more filter segments that may be replaceable. For example, in some implementations one or more filter segments may be replaceable in order to customize a user's experience with the device, including, for example, filter segments that provide different draw resistances and/or different flavors. Some examples of flavor adding materials and/or components configured to add a flavorant can be found in U.S. patent application Ser. No. 16/408,942, filed on May 10, 2019 and titled Flavor Article for an Aerosol Delivery Device; U.S. patent application Ser. No. 15/935,105, filed on Mar. 26, 2018, and titled Aerosol Delivery Device Providing Flavor Control; and U.S. patent application Ser. No. 16/353, 556, filed on Mar. 14, 2019, and titled Aerosol Delivery Device Providing Flavor Control, each of which is incorporated by reference herein in its entirety.

Preferably, the elements of the substrate material do not experience thermal decomposition (e.g., charring, scorching, or burning) to any significant degree, and the aerosolized components are entrained in the air drawn through the smoking article, including a filter (if present), and into the mouth of the user. In the smoking article 100 of the depicted implementation, the substrate material 516 comprises a plurality of tobacco beads together formed into a substantially cylindrical portion. In various implementations, however, the substrate material may comprise a variety of different compositions and combinations thereof, as explained in more detail below.

In various implementations, the substrate material may comprise a tobacco material, a non-tobacco material, or a combination thereof. In one implementation, for example, the substrate material may comprise a blend of flavorful and aromatic tobaccos in cut filler form. In another implementation, the substrate material may comprise a reconstituted tobacco material, such as described in U.S. Pat. No. 4,807, 809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety. For example, a reconstituted tobacco material may include a sheet-like material containing tobacco and/or tobacco-related materials. As such, in some implementations, the substrate material may be formed from a wound roll of a reconstituted tobacco material. In another implementation, the substrate material may be formed from shreds, strips, and/or the like of a reconstituted tobacco material. In another implementation, the tobacco sheet may comprise overlapping layers (e.g., a gathered web), which may, or may not, include heat conducting constituents. Examples of substrate portions that include a series of overlapping layers (e.g., gathered webs) of an initial substrate sheet formed by the fibrous filler material, aerosol forming material, and plurality of heat conducting constituents are described in U.S. patent application Ser. No. 15/905,320, filed on Feb. 26, 2018, and titled Heat Conducting Substrate For Electrically Heated Aerosol Delivery Device, which is incorporated herein by reference in its entirety.

In some implementations, the substrate material may include a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, one or more of the substrate materials may include a plurality of microcapsules each formed into a hollow cylindrical shape. In some implementations, one or more of the substrate materials may include a binder material configured to maintain the structural shape and/or integrity of the plurality of microcapsules formed into the hollow cylindrical shape.

Tobacco employed in one or more of the substrate materials may include, or may be derived from, tobaccos such as flue-cured tobacco, burley tobacco, Oriental tobacco, Maryland tobacco, dark tobacco, dark-fired tobacco and *Rustica* tobacco, as well as other rare or specialty tobaccos, or blends thereof. Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 6,730,832 to Dominguez et al.; U.S. Pat. No. 7,011,096 to Li et al.; U.S. Pat. No. 7,017,585 to Li et al.; U.S. Pat. No. 7,025,066 to Lawson et al.; U.S. Pat. App. Pub. No. 2004/0255965 to Perfetti et al.; PCT Pub. No. WO 02/37990 to Bereman; and Bombick et al., *Fund. Appl. Toxicol.*, 39, p. 11-17 (1997); the disclosures of which are incorporated herein by reference in their entireties.

In still other implementations of the present disclosure, the substrate material may include an extruded structure that includes, or is essentially comprised of a tobacco, a tobacco related material, glycerin, water, and/or a binder material, although certain formulations may exclude the binder material. In various implementations, suitable binder materials may include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethyl cellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass.

In some implementations, the substrate material may include an extruded material, as described in U.S. Pat. App. Pub. No. 2012/0042885 to Stone et al., which is incorporated herein by reference in its entirety. In yet another implementation, the substrate material may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents. In various implementations, the extruded material may have one or more longitudinal openings.

In various implementations, the substrate material may take on a variety of conformations based upon the various amounts of materials utilized therein. For example, a sample substrate material may comprise up to approximately 98% by weight, up to approximately 95% by weight, or up to approximately 90% by weight of a tobacco and/or tobacco related material. A sample substrate material may also comprise up to approximately 25% by weight, approximately 20% by weight, or approximately 15% by weight water—particularly approximately 2% to approximately 25%, approximately 5% to approximately 20%, or approximately 7% to approximately 15% by weight water. Flavors and the like (which include, for example, medicaments, such as nicotine) may comprise up to approximately 10%, up to about 8%, or up to about 5% by weight of the aerosol delivery component.

Additionally, or alternatively, the substrate material may include an extruded structure and/or a substrate that includes or essentially is comprised of tobacco, glycerin, water, and/or binder material, and is further configured to substantially maintain its structure throughout the aerosol-generating process. That is, the substrate material may be configured to substantially maintain its shape (e.g., the substrate material does not continually deform under an applied shear stress) throughout the aerosol-generating process. Although such an example substrate material may include liquids and/or some moisture content, the substrate may remain substantially solid throughout the aerosol-generating process and may substantially maintain structural integrity throughout the aerosol-generating process. Example tobacco and/or tobacco related materials suitable for a substantially solid substrate material are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are incorporated herein by reference in their entirety.

In some implementations, the amount of substrate material used within the smoking article may be such that the article exhibits acceptable sensory and organoleptic properties, and desirable performance characteristics. For example, in some implementations an aerosol precursor composition such as, for example, glycerin and/or propylene glycol, may be employed within the substrate material in order to provide for the generation of a visible mainstream aerosol that in many regards resembles the appearance of tobacco smoke. For example, the amount of aerosol precursor composition incorporated into the substrate material of the smoking article may be in the range of about 3.5 grams or less, about 3 grams or less, about 2.5 grams or less, about 2 grams or less, about 1.5 grams or less, about 1 gram or less, or about 0.5 gram or less.

According to another implementation, a smoking article according to the present disclosure may include a substrate material comprising a porous, inert material such as, for example, a ceramic material. For example, in some implementations ceramics of various shapes and geometries (e.g., beads, rods, tubes, etc.) may be used, which have various pore morphology. In addition, in some implementations non-tobacco materials, such as an aerosol precursor composition, may be loaded into the ceramics. In another implementation, the substrate material may include a porous, inert material that does not substantially react, chemically and/or physically, with a tobacco-related material such as, for example, a tobacco-derived extract. In addition, an extruded tobacco, such as those described above, may be porous. For example, in some implementations an extruded tobacco material may have an inert gas, such as, for example, nitrogen, that acts as a blowing agent during the extrusion process.

As noted above, in various implementations one or more of the substrate materials may include a tobacco, a tobacco component, and/or a tobacco-derived material that has been treated, manufactured, produced, and/or processed to incorporate an aerosol precursor composition (e.g., humectants such as, for example, propylene glycol, glycerin, and/or the like) and/or at least one flavoring agent, as well as a flame/burn retardant (e.g., diammonium phosphate and/or another salt) configured to help prevent ignition, pyrolysis, combustion, and/or scorching of the substrate material by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

As noted, in some implementations, flame/burn retardant materials and other additives that may be included within one or more of the substrate materials and may include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are suitable but are not preferred agents. In each aspect of flame-retardant, burn-retardant, and/or scorch-retardant materials used in the substrate material and/or other components (whether alone or in combination with each other and/or other materials), the desirable properties most preferably are provided without undesirable off-gassing or melting-type behavior.

According to other implementations of the present disclosure, the substrate material may also incorporate tobacco additives of the type that are traditionally used for the manufacture of tobacco products. Those additives may include the types of materials used to enhance the flavor and aroma of tobaccos used for the production of cigars, cigarettes, pipes, and the like. For example, those additives may include various cigarette casing and/or top dressing components. See, for example, U.S. Pat. No. 3,419,015 to Wochnowski; U.S. Pat. No. 4,054,145 to Berndt et al.; U.S. Pat. No. 4,887,619 to Burcham, Jr. et al.; U.S. Pat. No. 5,022,416 to Watson; U.S. Pat. No. 5,103,842 to Strang et al.; and U.S. Pat. No. 5,711,320 to Martin; the disclosures of which are incorporated herein by reference in their entireties. Preferred casing materials may include water, sugars and syrups (e.g., sucrose, glucose and high fructose corn syrup), humectants (e.g. glycerin or propylene glycol), and flavoring agents (e.g., cocoa and licorice). Those added components may also include top dressing materials (e.g., flavoring materials, such as menthol). See, for example, U.S. Pat. No. 4,449,541 to Mays et al., the disclosure of which is incorporated herein by reference in its entirety. Further materials that may be added include those disclosed in U.S. Pat. No. 4,830,028 to Lawson et al. and U.S. Pat. No. 8,186,360 to Marshall et al., the disclosures of which are incorporated herein by reference in their entireties.

In some implementations, the substrate material may comprise a liquid including an aerosol precursor composition and/or a gel including an aerosol precursor composition. Some examples of liquid compositions can be found in U.S. patent application Ser. No. 16/171,920, filed on Oct. 26, 2018, and titled Aerosol Delivery Device With Visible Indicator, which is incorporated herein by reference in its entirety.

As noted above, in various implementations, one or more of the substrate materials may have an aerosol precursor composition associated therewith. For example, in some implementations the aerosol precursor composition may comprise one or more different components, such as polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference. In some aspects, a substrate material may produce a visible aerosol upon the application of sufficient heat thereto (and cooling with air, if necessary), and the substrate material may produce an aerosol that is "smoke-like." In other aspects, the substrate material may produce an aerosol that is substantially non-visible but is recognized as present by other characteristics, such as flavor or texture. Thus, the nature of the produced aerosol may be variable depending upon the specific components of the aerosol delivery component. The substrate material may be chemically simple relative to the chemical nature of the smoke produced by burning tobacco.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally, or alternatively, include other active ingredients including, but not limited to, botanical ingredients (e.g., lavender, peppermint, chamomile, basil, rosemary, thyme, *eucalyptus*, ginger, *Cannabis, ginseng*, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)). It should be noted that the aerosol precursor composition may comprise any constituents, derivatives, or combinations of any of the above.

As noted herein, the aerosol precursor composition may comprise or be derived from one or more botanicals or constituents, derivatives, or extracts thereof. As used herein, the term "botanical" includes any material derived from plants including, but not limited to, extracts, leaves, bark, fibres, stems, roots, seeds, flowers, fruits, pollen, husk, shells or the like. Alternatively, the material may comprise an active compound naturally existing in a botanical, obtained synthetically. The material may be in the form of liquid, gas, solid, powder, dust, crushed particles, granules, pellets, shreds, strips, sheets, or the like. Example botanicals are tobacco, *eucalyptus*, star anise, hemp, cocoa, *Cannabis*, fennel, lemongrass, peppermint, spearmint, rooibos, chamomile, flax, ginger, *Ginkgo biloba*, hazel, hibiscus, laurel, licorice (liquorice), matcha, mate, orange skin, *papaya*, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, *curcuma*, turmeric, sandalwood, cilantro, bergamot, orange blossom, myrtle, cassis, valerian, pimento, mace, damien, marjoram, olive, lemon balm, lemon basil, chive, *carvi, verbena*, tarragon, geranium, mulberry, *ginseng*, theanine, theacrine, maca, ashwagandha, damiana, guarana, chlorophyll, baobab or any combination thereof. The mint may be chosen from the following mint varieties: *Mentha* Arventis, *Mentha* c.v., *Mentha niliaca, Mentha piperita, Mentha piperita citrata* c.v., *Mentha piperita* c.v, *Mentha spicata crispa, Mentha cardifolia, Mentha longifolia, Mentha suaveolens variegata, Mentha pulegium, Mentha spicata* c.v. and *Mentha suaveolens*.

A wide variety of types of flavoring agents, or materials that alter the sensory or organoleptic character or nature of the mainstream aerosol of the smoking article may be suitable to be employed. In some implementations, such flavoring agents may be provided from sources other than tobacco and may be natural or artificial in nature. For example, some flavoring agents may be applied to, or incorporated within, the substrate material and/or those regions of the smoking article where an aerosol is generated. In some implementations, such agents may be supplied directly to a heating cavity or region proximate to the heat source or are provided with the substrate material. Example flavoring agents may include, for example, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, may also be suitable to be employed.

As used herein, the terms "flavor," "flavorant," "flavoring agents," etc. refer to materials which, where local regulations permit, may be used to create a desired taste, aroma, or other somatosensorial sensation in a product for adult consumers. They may include naturally occurring flavor materials, botanicals, extracts of botanicals, synthetically obtained materials, or combinations thereof (e.g., tobacco, *Cannabis*, licorice (liquorice), *hydrangea*, eugenol, Japanese white bark *magnolia* leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, *papaya*, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, *betel*, shisha, pine, honey essence, rose oil, vanilla, lemon oil, orange oil, orange blossom, cherry blossom, *cassia*, caraway, cognac, jasmine, ylang-ylang, sage, fennel, wasabi, piment, ginger, coriander, coffee, hemp, a mint oil from any species of the genus *Mentha, eucalyptus*, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, *curcuma*, cilantro, myrtle, cassis, valerian, pimento, mace, damien, marjoram, olive, lemon balm, lemon basil, chive, *carvi, verbena*, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, liquid such as an oil, solid such as a powder, or gas.

In some implementations, the flavor comprises menthol, spearmint, and/or peppermint. In some embodiments, the flavor comprises flavor components of cucumber, blueberry, citrus fruits, and/or redberry. In some embodiments, the flavor comprises eugenol. In some embodiments, the flavor comprises flavor components extracted from tobacco. In some embodiments, the flavor comprises flavor components extracted from *Cannabis*.

In some implementations, the flavor may comprise a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to eucolyptol, WS-3.

Flavoring agents may also include acidic or basic characteristics (e.g., organic acids, such as levulinic acid, succinic acid, pyruvic acid, and benzoic acid). In some implementations, flavoring agents may be combinable with the elements of the substrate material if desired. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. Any of the materials, such as flavorings, casings, and the like that may be useful in combination with a tobacco material to affect sensory properties thereof, including organoleptic properties, such as described herein, may be combined with the substrate material. Organic acids particularly may be able to be incorporated into the substrate material to affect the flavor, sensation, or organoleptic properties of medicaments, such as nicotine, that may be able to be combined with the substrate material. For example, organic acids, such as levulinic acid, lactic acid, pyruvic acid, and benzoic acid may be included in the substrate material with nicotine in amounts up to being equimolar (based on total organic acid content) with the nicotine. Any combination of organic acids may be suitable. For example, in some implementations, the substrate material may include approximately 0.1 to about 0.5 moles of levulinic acid per one mole of nicotine, approximately 0.1 to about 0.5 moles of pyruvic acid per one mole of nicotine, approximately 0.1 to about 0.5 moles of lactic acid per one mole of nicotine, or combinations thereof, up to a concentration wherein the total amount of organic acid present is equimolar to the total amount of nicotine present in the substrate material. Various additional examples of organic acids employed to produce a substrate material are described in U.S. Pat. App. Pub. No. 2015/0344456 to Dull et al., which is incorporated herein by reference in its entirety.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In other implementations, the substrate material may include other materials having a variety of inherent characteristics or properties. For example, the substrate material may include a plasticized material or regenerated cellulose in the form of rayon. As another example, viscose (commercially available as VISIL®), which is a regenerated cellulose product incorporating silica, may be suitable. Some carbon fibers may include at least 95 percent carbon or more. Similarly, natural cellulose fibers such as cotton may be suitable, and may be infused or otherwise treated with silica, carbon, or metallic particles to enhance flame-retardant properties and minimize off-gassing, particularly of any undesirable off-gassing components that would have a negative impact on flavor (and especially minimizing the likelihood of any toxic off-gassing products). Cotton may be treatable with, for example, boric acid or various organophosphate compounds to provide desirable flame-retardant properties by dipping, spraying or other techniques known in the art. These fibers may also be treatable (coated, infused, or both by, e.g., dipping, spraying, or vapor-deposition) with organic or metallic nanoparticles to confer the desired property of flame-retardancy without undesirable off-gassing or melting-type behavior.

In the depicted implementation, the substrate material 516 may comprise a centrally defined longitudinally extending axis between the opposed first and second ends, and a cross-section of the substrate material 516 may be, in some implementations, symmetrical about the axis. For example, in some implementations a cross-section of the substrate material may be substantially circular such that the substrate material defines a substantially cylindrical shape extending between the opposed first and second ends thereof. However, in other implementations, the substrate material may define a substantially non-circular cross-section such that the substrate material may define a substantially non-cylindrical shape between the opposed first and second ends thereof. Otherwise, in other examples, the substrate material may comprise an asymmetric cross-section about the axis. In various implementations, each end of the substrate material may be in axial alignment with adjacent elements.

As shown in FIGS. 7 and 8, the outer housing 512 of the cartridge 500 of the depicted implementation is configured to circumscribe at least a portion of the substrate portion 510, including the substrate material 516. In the depicted implementation, the outer housing 512 is also configured to circumscribe at least a portion of the heat source 508. In some implementations, the outer housing may circumscribe the entire heat source. In the depicted implementation, the outer housing comprises a rigid material. For example, the outer housing 512 of the depicted implementation is constructed of an aluminum material; however, in other implementations the outer housing may be constructed of other materials, including other metal materials (such as, for example, stainless steel, aluminum, brass, copper, silver, gold, and bronze), or graphite materials, or ceramic materials, or plastic materials, or any combinations thereof. In some implementations, at least a portion of the heat source and/or at least a portion of the substrate material may be circumscribed by a paper foil laminate. In some implementations, the cartridge may comprise an enclosure comprising a laminate that contains a heat source and a beaded substrate material. Some examples of laminates and/or enclosures that may be applicable to the present disclosure can be found in U.S. patent application Ser. No. 16/174,846, filed on Oct. 30, 2018, and titled Smoking Article Cartridge, which is incorporated herein by reference in its entirety.

In the depicted implementation, the outer housing 512 is constructed as tube structure that substantially encapsulates the substrate material 516; however, as noted above, in other implementations the outer housing may have other shapes. Although the shape of the outer housing may vary, in the depicted implementation the outer housing 512 comprises a tube structure having an open end and a closed end. The depicted implementation of the outer housing 512 also includes one or more end apertures 518 located on the closed end of the outer housing 512 that are configured to allow aerosolized vapor (herein alternatively referred to as a "vapor" or "aerosol") to pass therethrough. The end apertures 518 of the depicted implementation are in the form of a pair of elongate rounded slots; however, in other implementations the end apertures may have any form that permits passage of the aerosol therethrough. As such, it will be appreciated that the end apertures 518 can comprise fewer or additional apertures and/or alternative shapes and sizes of apertures than those illustrated.

As described above, in the holder of the present invention is configured to move to and from an open position and a use position. In various implementations, the open position is configured to allow a user to insert and remove a cartridge. It should be noted that in other implementations, the holder of the present disclosure may include a third position, which may be an extinguishment position. In such a manner, the extinguishment position may be configured such that the heat source is deprived of sufficient oxygen to sustain combustion. In some implementations, the extinguishment position may be obtained by a further action of the second body portion. In other implementations, for example, one or more additional features may be included such that an extinguishment position may be achieved by actuating the one or more additional features. In particular, in one implementation the device may include an air impermeable cover feature located proximate the distal end of the second body portion that may be mechanically or manually actuatable (e.g., by rotating the cover feature over the end of the second body portion and/or by sliding the cover feature across the end of the second body portion) such that in the extinguishment position, the cover feature substantially covers the open end of the second body portion and the heat source is deprived of sufficient oxygen to sustain combustion. In another implementation, the device may include a detachable feature, such as, for example an end cap, that may be used to achieve the extinguishment position. For example, in some implementations a separate end cap may be attachable over the distal end of the second body portion such that, once attached, the heat source is deprived of sufficient oxygen to sustain combustion. Such an end cap could also be used to cover the end of the second body portion when not in use, such as, for example, to prevent dirt and/or foreign objects from entering into the device. Additionally, or alternatively, in some implementations the holder of the present disclosure may include an air permeable cover feature (e.g., a cover feature comprising a plurality of openings or a cover feature comprising a mesh) that protects the heat source in the use position. For example, in one implementation the holder may include an air permeable cover feature located proximate the distal end of the second body portion that may be mechanically or manually actuatable (e.g., by rotating the cover feature over the end of the second body portion and/or by sliding the cover feature across the end of the second body portion) such that once ignited, the cover feature may be actuated to substantially cover the open end of the second body portion while maintaining sufficient access of oxygen to the heat source.

In the depicted implementation, the first body portion 300 (including the guide post 306) and the second body portion 400 include walls that are substantially solid and non-porous; however, in other implementations one or more of these walls may have other configurations. For example, in some implementations one or more of the walls of the first body portion, guide post, or second body portion may be non-solid and/or substantially porous or may include one or more non-solid and/or substantially porous portions. In some implementations, for example, the second body portion may include one or more apertures that may facilitate access of oxygen to the heat source. Alternatively, or additionally, other implementations may include one or more apertures that may mix with the aerosol generated during a draw. In such a manner, in the use position the one or more apertures may be located proximate the heat source, thus providing the heat source with additional access to oxygen during combustion. In some implementations, the guide post and/or the first body portion may include one or more apertures. For example, in some implementations the guide post and/or the first body portion may include apertures that extend into the aerosol passage of the first body portion such that air from outside the holder may mix with aerosol generated by the substrate material.

In some implementations, the holder (e.g., the guide post and/or the second body portion) may include detent features configured to locate the second body portion in the open position and/or the use position. In some implementations, the holder may include one or more magnets configured to bias and/or locate the second body portion in the open position and/or the use position. In some implementations, the holder may include one or more additional spring features configured to bias and/or locate the second body portion in the open position and/or the use position. In some further implementations, the holder may emit an audible click when the sleeve is positioned in the open position and/or the use position.

In various implementations, the present disclosure may be directed to kits that provide a variety of components as described herein. For example, a kit may comprise a holder with one or more cartridges. In another implementation, a kit may comprise a plurality of holders. In further implementations, a kit may comprise a plurality of cartridges. In yet another implementation, a kit may comprise a plurality of holders and a plurality of cartridges. The inventive kits may further include a case (or other packaging, carrying, or storage component) that accommodates one or more of the further kit components. The case could be a reusable hard or soft container. Further, the case could be simply a box or other packaging structure. In some implementations, a brush or other cleanout accessory may be included in a kit. The cleanout accessory may be configured to be inserted in a receiving chamber of the holder, or, in other implementations, inserted in a separate aperture that enables a user to remove debris from the receiving chamber.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A holder for use with a removable and replaceable substrate cartridge, the holder comprising:
    a first body portion defining a main body and a guide post extending from the main body, the guide post defining a distal end, and the main body defining an opposite mouth end, the guide post further defining a receiving chamber extending at least a portion therethrough; and
    a second body portion,
    wherein the second body portion is configured to rotate about and slide along at least a portion of the guide post to and from at least:
        a use position, wherein the second body portion is proximate the main body of the first body portion and the substrate cartridge is retained in the receiving chamber, and
        an open position, wherein the second body portion is rotated relative to and extended away from the main body of the first body portion such that the substrate cartridge can be inserted into or removed from the receiving chamber;
    wherein the second body portion is biased in the open position relative to the main body of the first body portion.

2. The holder of claim 1, wherein the guide post includes a guide slot, wherein the second body portion includes a guide pin, and wherein the guide pin is configured to move within the guide slot to and from the use position and the open position.

3. The holder of claim 1, wherein the guide post has a substantially cylindrical shape.

4. The holder of claim 1, wherein the second body portion includes a rotation limitation feature and the first body portion includes an extension slot.

5. The holder of claim 1, wherein the second body portion includes a pair of openings proximate a distal end thereof.

6. The holder of claim 1, wherein at least one of the first body portion or the second body portion includes a cartridge retention feature.

7. The holder of claim 6, wherein the cartridge retention feature comprises one or more retention spheres disposed in the guide post.

8. The holder of claim 1, wherein at least one of first body portion or the second body portion has a substantially oblong overall shape.

9. A holder for use with a removable and replaceable substrate cartridge, the holder comprising:
a first body portion defining a main body and a guide post extending from the main body, the guide post defining a distal end, and the main body defining an opposite mouth end, the guide post further defining a receiving chamber extending at least a portion therethrough; and
a second body portion,
wherein the second body portion is configured to rotate about and slide along at least a portion of the guide post to and from at least:
a use position, wherein the second body portion is proximate the main body of the first body portion and the substrate cartridge is retained in the receiving chamber, and
an open position, wherein the second body portion is rotated relative to and extended away from the main body of the first body portion such that the substrate cartridge can be inserted into or removed from the receiving chamber,
wherein at least one of the first body portion or the second body portion includes a cartridge retention feature,
wherein the cartridge retention feature comprises one or more retention spheres disposed in the guide post, and
wherein the cartridge retention feature further comprises one or more corresponding cam surfaces located on an inner surface of the second body portion.

10. An aerosol delivery device comprising:
a removable cartridge comprising a substrate portion that includes a substrate material having an aerosol precursor composition configured to form an aerosol upon application of heat thereto; and
a holder comprising a first body portion defining a main body and a guide post extending from the main body, the guide post defining a distal end, and the main body defining an opposite mouth end, the guide post further defining a receiving chamber extending at least a portion therethrough, and a second body portion,
wherein the second body portion is configured to rotate about and slide along at least a portion of the guide post to and from at least:
a use position, wherein the second body portion is proximate the main body of the first body portion and the cartridge is retained in the receiving chamber, and
an open position, wherein the second body portion is rotated relative to and extended away from the main body of the first body portion such that the cartridge can be inserted into or removed from the receiving chamber;
wherein the second body portion is biased in the open position relative to the main body of the first body portion.

11. The aerosol delivery device of claim 10, wherein the guide post includes a guide slot, wherein the second body portion includes a guide pin, and wherein the guide pin is configured to move within the guide slot to and from the use position and the open position.

12. The aerosol delivery device of claim 10, wherein the guide post has a substantially cylindrical shape.

13. The aerosol delivery device of claim 10, wherein the second body portion includes a rotation limitation feature and the first body portion includes an extension slot.

14. The aerosol delivery device of claim 10, wherein the second body portion includes a pair of openings proximate a distal end thereof, which are also configured to be proximate the heat source of the cartridge when in the use position.

15. The aerosol delivery device of claim 10, wherein at least one of the first body portion or the second body portion includes a cartridge retention feature.

16. The aerosol delivery device of claim 15, wherein the cartridge retention feature comprises one or more retention spheres disposed in the guide post.

17. The aerosol delivery device of claim 10, wherein at least one of first body portion or the second body portion has a substantially oblong overall shape.

18. The aerosol delivery device of claim 10, wherein the cartridge further comprises a heat portion including a heat source configured to generate heat.

19. The aerosol delivery device of claim 18, wherein the substrate portion is disposed proximate the heat source.

20. An aerosol delivery device comprising:
a removable cartridge comprising a substrate portion that includes a substrate material having an aerosol precursor composition configured to form an aerosol upon application of heat thereto; and
a holder comprising a first body portion defining a main body and a guide post extending from the main body, the guide post defining a distal end, and the main body defining an opposite mouth end, the guide post further defining a receiving chamber extending at least a portion therethrough, and a second body portion,
wherein the second body portion is configured to rotate about and slide along at least a portion of the guide post to and from at least:
a use position, wherein the second body portion is proximate the main body of the first body portion and the cartridge is retained in the receiving chamber, and
an open position, wherein the second body portion is rotated relative to and extended away from the main body of the first body portion such that the cartridge can be inserted into or removed from the receiving chamber,
wherein at least one of the first body portion or the second body portion includes a cartridge retention feature,
wherein the cartridge retention feature comprises one or more retention spheres disposed in the guide post,
wherein the cartridge retention feature further comprises one or more corresponding cam surfaces located on an inner surface of the second body portion.

* * * * *